US011389469B2

(12) United States Patent
Wu et al.

(10) Patent No.: US 11,389,469 B2
(45) Date of Patent: Jul. 19, 2022

(54) TARGETING NAD+ TO TREAT CHEMOTHERAPY AND RADIOTHERAPY INDUCED COGNITIVE IMPAIRMENT, NEUROPATHIES AND INACTIVITY

(71) Applicant: NewSouth Innovations Pty Ltd, Sydney (AU)

(72) Inventors: Lindsay Edward Wu, Coogee (AU); David A. Sinclair, Chestnut Hill, MA (US)

(73) Assignee: NewSouth Innovations Pty Ltd, Sydney (AU)

(*) Notice: Subject to any disclaimer, the term of this patent is extended or adjusted under 35 U.S.C. 154(b) by 0 days.

(21) Appl. No.: 16/790,965

(22) Filed: Feb. 14, 2020

(65) Prior Publication Data

US 2020/0405736 A1    Dec. 31, 2020

Related U.S. Application Data

(62) Division of application No. 15/570,210, filed as application No. PCT/US2016/029765 on Apr. 28, 2016, now Pat. No. 10,603,334.

(60) Provisional application No. 62/153,876, filed on Apr. 28, 2015.

(51) Int. Cl.
| *A61K 31/706* | (2006.01) |
| *A61K 38/45* | (2006.01) |
| *A61K 31/455* | (2006.01) |
| *A61K 31/443* | (2006.01) |
| *A61K 31/7076* | (2006.01) |
| *A61K 31/52* | (2006.01) |
| *A61P 25/02* | (2006.01) |

(52) U.S. Cl.
CPC .......... *A61K 31/706* (2013.01); *A61K 31/443* (2013.01); *A61K 31/455* (2013.01); *A61K 31/52* (2013.01); *A61K 31/7076* (2013.01); *A61K 38/45* (2013.01); *A61P 25/02* (2018.01); *C12Y 204/02012* (2013.01); *C12Y 207/07001* (2013.01)

(58) Field of Classification Search
CPC .. A61K 31/706; A61K 31/52; A61K 31/7076; A61K 31/443; A61K 31/455; A61P 25/02
See application file for complete search history.

(56) References Cited

U.S. PATENT DOCUMENTS

| 7,012,086 B1 | 3/2006 | Murray |
| 7,737,158 B2 | 6/2010 | Imai et al. |
| 8,106,184 B2 | 1/2012 | Sauve et al. |
| 8,148,338 B2 | 4/2012 | Klinski et al. |
| 8,604,074 B2 | 12/2013 | McKnight et al. |
| 10,603,334 B2 | 3/2020 | Wu et al. |
| 2006/0002914 A1 | 1/2006 | Milbrandt et al. |
| 2006/0229265 A1 | 10/2006 | Milburn et al. |
| 2007/0117765 A1 | 5/2007 | Sauve et al. |
| 2011/0052676 A1 | 3/2011 | Gruber |
| 2012/0172584 A1 | 7/2012 | Sauve et al. |
| 2012/0328526 A1 | 12/2012 | Kristian |
| 2016/0279161 A1 | 9/2016 | Wu et al. |

FOREIGN PATENT DOCUMENTS

| CN | 1695635 A | 11/2005 |
| CN | 102631385 A | 8/2012 |
| CN | 102973461 A | 3/2013 |
| WO | WO-2001/064211 A1 | 9/2001 |
| WO | WO-2006/001982 A2 | 1/2006 |
| WO | WO-2006/066244 A2 | 6/2006 |
| WO | WO-2008/011364 A2 | 1/2008 |
| WO | WO-2009/108999 A1 | 9/2009 |
| WO | WO-2009/113984 A1 | 9/2009 |
| WO | WO-2012/068539 A1 | 5/2012 |
| WO | WO-2013/090645 A1 | 6/2013 |
| WO | WO-2014/038873 A1 | 3/2014 |
| WO | WO-2014/107730 A2 | 7/2014 |
| WO | WO-2014/152864 A1 | 9/2014 |
| WO | WO-2015/070280 A1 | 5/2015 |
| WO | WO-2016/176437 A1 | 11/2016 |

OTHER PUBLICATIONS

Pickles et al., Radiotherapy and Oncology, 1996, 40, p. 245-247. (Year: 1996).*
Surjana et al., Journal of Investigative Dermatology, 2012, 132, p. 1497-1500. (Year: 2012).*
Ashok et al., "Amelioration of diabetes-induced neurobehavioral and neurochemical changes by melatonin and nicotinamide: Implication of oxidative stress-PARP pat," Pharmacology Biochemistry and Behavior, 114:43-51 (2013).
Camandola et al., "Aberrant subcellular neuronal calcium regulation in aging and Alzheimer's disease," Molecular Cell Research, 1813(5):965-973 (2010).
Chang et al., "Nicotinamide adenine dinucleotide (NAD)-regulated DNA methylation alters CCTC-binding factor (CTCF)/cohesin binding and transcription at the BDNF locus," Proceedings of the National Academy of Sciences, 107(50):21836-21841 (2010).
Extended European Search Report received for EP Patent Application No. 16787140, dated Sep. 20, 2018.
International Search Report and Written Opinion for International Application No. PCT/US16/29765 dated Sep. 23, 2016.
Janelsins et al., "An update on cancer- and chemotherapy-related cognitive dysfunction: current status," Semin Oncol, 38(3):431-438 (2011).

(Continued)

*Primary Examiner* — Jonathan S Lau
(74) *Attorney, Agent, or Firm* — Foley Hoag LLP; David P. Halstead

(57) ABSTRACT

Methods and compositions for preventing or treating peripheral neuropathy, cognitive deficits, inactivity, depression, chemotherapy and/or radiotherapy induced peripheral neuropathy and cognitive deficits, and improving cognitive performance, in a subject in need thereof are disclosed. The disclosed methods include the step of administering to the subject an effective amount of an agent that increases the level of NAD$^+$ in the subject.

14 Claims, 3 Drawing Sheets

(56) References Cited

OTHER PUBLICATIONS

Lussier et al., "Adjuvant analgesics in cancer pain management," Oncologist, 9(5):571-591 (2004).
Oxford English Dictionary Online, "prevent," Oxford University Press, http://dictionary.oed.com/ (2010).
Raffa et al., "Chemo Fog: Cancer Chemotherapy-Related Cognitive Impairment" Springer-Verlag New York. 2010. pp. 147-156.
Stone et al., "Cancer-treatment-induced neurotoxicity—focus on newer treatments," Nat. Rev. Clin. Oncol. 13:92-105 (2016).
Wang, "Pathophysiology of cancer-related fatigue," Clin J Oncol Nurs, 12(5 Suppl):11-20 (2008).
Anderson et al., "Manipulation of a Nuclear NAD+ Salvage Pathway Delays Aging without Altering Steady-state NAD+ Levels," J Biol Chem, 277(21) 18881-18890 (2002).
Begum et al., "Apigenin Ameliorated Gamma Radiation-Induced Cytogenetic Alterations in Cultured Human Blood Lymphocytes," Mutat Res-Gen Tox En, 747(1): 71-76 (2012) [abstract only].
Burd et al., "Monitoring Tumorigenesis and Senescence in Vivo with a p16INK4a-Luciferase Model," Cell, 152(0): 340-351 (Jan. 2013).
Celia et al., "Patient-reported peripheral neuropathy of doxorubicin and cisplatin with and without paclitaxel in the treatment of advanced endometrial cancer: Results from GOG 184," Gynecologic Oncology, 119:538-542 (2010).
Chung et al., "Regulation of SIRT1 in Cellular Functions: Role of Polyphenols," Arch Biochem Biophys, 501(1): 79-90 (2010).
Coppe et al., "The Senescence-Associated Secretory Phenotype: The Dark Side of Tumor Suppression," Annu Rev Pathol, 5: 99-118 (2010).
De Souza, "Primer: Genome Editing with Engineered Nucleases," Nat Methods, 9(1): 27 (Jan. 2012).
Debacq-Chainiaux et al., "Protocols to Detect Senescence-Associated Beta-Galactosidase (SA-Betagal) Activity, a Biomarker of Senescent Cells in Culture and In Vivo," Nat Protoc, 4(12): 1798-1806 (2009).
Devipriya et al., "Quercetin Ameliorates Gamma Radiation-Induced DNA Damage and Biochemical Changes in Human Peripheral Blood Lymphocytes," Mutut Res-Gen Tox En, 654(1): 1-7 (2008) [abstract only].
Escande et al., "Flavonoid Apigenin is an Inhibitor of the NAD+ase CD38," Diabetes, 62: 1084-1093 (Apr. 2013).
Extended European Search Report issued by the European Patent Office in corresponding Application No. 14863002.3, dated Aug. 4, 2017.
International Search Report issued by the International Searching Authority in corresponding International Application No. PCT/AU2014/001048, dated Jan. 22, 2015.
Kim et al., "Augmentation of NAD+ by NQO1 Attenuates Cisplatin-Mediated Hearing Impairment," Cell Death and Disease, 5(e1292): 1-13 (2014).
Kim et al., "NAD+ Metabolism in Age-Related Hearing Loss," Aging and Disease, 5(2): 150-159 (Apr. 2014).
Krishnamurthy et al., "Ink4a/Arf Expression is a Biomarker of Aging," J Clin Invest, 114(9): 1299-1307 (Nov. 2004).
Kuilman et al., "The Essence of Senescence," Gen Dev, 24: 2463-2479 (2010).
Lin et al., "Combination of Quercetin with Radiotherapy Enhances Tumor Radiosensitivity in Vitro and in Vivo," Radiother Oncol, 104(3): 395-400 (2012) [abstract only].
Lu, "Beta-lapachone Ameliorates Murine Cisplatin Nephrotoxicty—NAD+, NQO1, and SIRT1 at the Crossorads of Metabolism, Injury, and Inflammation," Kidney Int, 85(3): 496-498 (Mar. 2014).
Oh et al., "Pharmacological Activation of NQO1 Increases NAD+ Levels and Attenuates Cisplatin-Mediated Acute Kidney Injury in Mice," Kidney Int, 85: 547-560 (2014).
Reagan-Shaw et al., "Dose Translation from Animal to Human Studies Revisited," FASEB J, 22: 659-661 (2007).
Rithidech et al., "Protective effect of apigenin on radiation-induced chromosomal damage in human lymphocytes," Mutat Res-Gen Tox En, 585(1-2): 96-104 (2005).
Sauve et al., "Sir2 Regulation by Nicotinamide Results from Switching between Base Exchange and Deacetylation Chemistry," Biochemistry, 42(31): 9249-9256 (Aug. 2003).
Schwartz et al., "The Effect of Growth Conditions on NAD+ and NADH Concentrations and the NAD+: NADH Ratio in Normal and Transformed Fibroblasts," J Biol Chem, 249(13): 4138-4143 (1974).
Smith et al., "A Combinatorial Approach to Create Artificial Homing Endonucleases Cleaving Chosen Sequences," Nucelic Acids Res, 34(22): e149 (2006).
Sorrentino et al., "p16INK4a Reporter Mice Reveal Age-Promoting Effects of Environmental Toxicants," J Clin Invest, 124(1): 169-173 (Jan. 2014).
Supplementary Partial European Search Report issued by the European Patent Office in corresponding International Application No. PCT/AU2014/001048, dated May 2, 2017.
Tan et al., "Precision Editing of Large Animal Genomes," Adv Genet, 80: 37-97 (2012).
Umov et al., "Genome Editing with Engineered Zinc Finger Nucleases," Nat Rev Genet, 11(9): 636-646 (Sep. 2010).
Wang et al., "P7C3 Neuroprotective Chemicals Function by Activiating the Rate-Limiting Enzyme in NAD Salvage," Cell, 158(6): 1324-1334 (2014).
Yamada et al., "The Simultaneous Measurement of Nicotinamide Adenine Dinucleotide and Related Compounds by Liquid Chromatrography/Electrospray Ionization Tandem Mass Spectrometry," Anal Biochem, 352: 282-285 (2006).
Yan et al., "Quercetin Inhibits Left Ventricular Hypertrophy in Spontaneously Hypertensive Rats and Inhibits Angiotensin II-induced H9C2 Cells Hypertrophy by Enhancing PPAR-γ Expression and Suppressing AP-1 Activity," PLOS One, 8(9): e72548 (2013).
Yang et al., "Quercetin-3-O-β-D-glucuronide Isolated from Polymgonum aviculare Inhibits Cellular Senescence in Human Primary Cells," Arch Pharm Res, 37: 1219-1233 (2014).
Yoshino et al., "Nicotinamide mononucleotide, a key NAD+ intermediate, treats the pathophysiology of diet- and age-induced diabetes in mice," Cell Metabolism, 5:528-536 (2011).

* cited by examiner

TARGETING NAD+ TO TREAT CHEMOTHERAPY AND RADIOTHERAPY INDUCED COGNITIVE IMPAIRMENT, NEUROPATHIES AND INACTIVITY

CROSS-REFERENCE TO RELATED APPLICATIONS

This application is a divisional of U.S. patent application Ser. No. 15/578,210 filed Oct. 27, 2017, which is the U.S. National Stage Application of PCT/US2016/029765, filed Apr. 28, 2016, which claims the benefit of U.S. Patent Application Ser. No. 62/153,876, filed Apr. 28, 2015, each of which is incorporated by reference herein as if set forth in its entirety.

STATEMENT REGARDING FEDERALLY SPONSORED RESEARCH OR DEVELOPMENT

Not applicable.

BACKGROUND

It is well-known that chemotherapy and radiotherapy can be neurotoxic, producing neural damage that can result in neuropathies and/or cognitive impairments. A significant subset of cancer survivors report ongoing cognitive problems after treatment, highlighting difficulties with memory, working memory and attention [2]. The consequent impact on daily function, return to work and quality of life has been described as the most troublesome survivorship issue that patients face [3]. Such chemotherapy-induced cognitive impairments (CICI) have been verified in several ways. First, objective neuropsychological testing indicates impairment in processing speed, attention/concentration, executive function, and verbal and visual memory in 17-50% of survivors, which persist for years post-treatment [4]. Second, neuroimaging studies of cancer survivors have correlated impaired performance in memory and executive function tasks with alterations in brain morphology and activation patterns in areas important for these tasks, such as the hippocampus and pre-frontal cortices [5, 6], and with extensive white matter abnormalities associated with cognitive impairment [7].

Further evidence shows that chemotherapy and radiotherapy have neurotoxic side-effects. Many patients develop painful and disabling neuropathies during chemotherapy, especially those receiving taxanes, such as docetaxel, and platinum compounds, such as oxaliplatin. Estimates vary, with between 70-90% of patients experiencing chemotherapy-induced peripheral neuropathies (CIPN) during treatment [8]. CIPN can present as a progressive and enduring tingling numbness, intense pain and hypersensitivity to cold and touch, beginning in the hands and feet and sometimes involving the arms and legs. CIPN is a significant source of distress during treatment, and can be the rate-limiting factor in treatment leading to either dose reduction or, in rare cases, cessation of chemotherapy. These effects are lasting. At 6 months after treatment, 30% of patients continue to experience CIPN [8] and are irreversible in 10-20% of patients [9]. CIPN has clear severe negative effects on patients' quality of life, sleep and mood after treatment [9].

Importantly, impairments in cognitive testing can occur in the absence of changes in locomotor activity, or anxiety, anhedonia or depressive-like behaviours [16]. Moreover, the cognitive impairments persist longer than allodynia in laboratory rats, indicating that poor performance in cognitive testing is not related to disability associated with pain [11].

Chemotherapy can lead to inactivity, malaise and lethargy, which can contribute to a downward spiral in health. Interventions that increase voluntary activity could alleviate this, and improve physical, neurological and mental health of cancer survivors.

Chemotherapy can lead to depression, anxiety, circadian rhythm disorders including impaired sleep, mental health issues, neuropsychiatric and neuropsychological disorders, which can impair quality of life for cancer survivors.

$NAD^+$ levels decline with age [17], and are raised by calorie restriction and exercise in humans and in rodents. Interventions that raise $NAD^+$ (e.g., calorie restriction and exercise) have been shown to reduce cancer risk and prevent tumor growth [19, 20], and reduce CIPN and CICI [42].

The $NAD^+$ precursors nicotinamide mononucleotide (NMN) and nicotinamide riboside (NR) have been shown to improve metabolism and reverse aspects of ageing in elderly mice [17].

Axon degeneration occurs frequently in neurodegenerative diseases and peripheral neuropathies. The degeneration of transected axons is delayed in Wallerian degeneration slow (Wlds) mice with the overexpression of a fusion protein with the nicotinamide adenine dinucleotide ($NAD^+$) synthetic enzyme, nicotinamide mononucleotide adenylyltransferase (Nmnat1). Both Wld(s) and Nmnat1 themselves are functional in preventing axon degeneration in neuronal cultures.

$NAD^+$ levels decrease in injured, diseased, or degenerating neural cells (Araki et al Science 2004).

In summary, anti-cancer treatment with chemotherapy and/or radiotherapy has delivered increased survival rates for many cancers, at the cost of severe side effects that have a meaningful impact on survivor quality of life, which in the case of CIPN and cognitive impairment impact the feasibility of ongoing treatment. Thus, there is a need for new therapeutic strategies to treat or prevent chemotherapy and/or radiotherapy induced cognitive impairment and/or neuropathies.

Neuronal injury or impairment can have a variety of causes.

Neuronal injury can cause cognitive deficits such as decreased memory, slower processing speed, decreased concentration/attention, impaired spatial, verbal and visual memory, impaired executive function, impaired social interactions, impaired verbal and non-verbal communication, and impaired social interaction.

Neuronal injury can further cause mental health disorders such as depression, anxiety, risk of self harm and suicide, substance addiction and abuse.

BRIEF SUMMARY

In one aspect, the present invention discloses a method for preventing, treating or providing increased resistance to neuropathy and/or pain; and associated disorders including cramps, neuromuscular paralysis, loss of sensation/numbness, tingling feeling, loss of motor skills, sexual dysfunction in a subject. The method comprises administering to the subject an effective amount of an agent that increases the level of $NAD^+$ in the subject.

In another aspect, the present invention is a method for improving cognitive function, including memory, processing speed, executive function, attention, concentration, and overall intelligence in a subject. The method comprises administering to the subject an effective amount of an agent that increases the level of NAD$^+$ in the subject.

In another aspect, the present invention is a method for preventing or treating cognitive deficits, neurocognitive deficits and/or neurodevelopmental disorders in a subject. The method comprises administering to the subject an effective amount of an agent that increases the level of NAD$^+$ in the subject.

In another aspect, the present invention is a method for increasing voluntary activity, increased endurance and stamina in a subject. The method comprises administering to the subject an effective amount of an agent that increases the level of NAD$^+$ in the subject.

In another aspect, the present invention is a method for preventing or treating inactivity, malaise, lethargy, and melancholy in a subject in need thereof. The method comprises administering to the subject an effective amount of an agent that increases the level of NAD$^+$ in the subject.

In another aspect, the present invention is a method for preventing or treating depression, anxiety, post-traumatic stress disorder, and other mental health and psychological disorders in a subject. The method comprises administering to the subject an effective amount of an agent that increases the level of NAD$^+$ in the subject.

In another aspect, the present invention is a method for preventing or treating sexual dysfunction associated with nerve damage and/or impairment in a subject. The method comprises administering to the subject an effective amount of an agent that increases the level of NAD$^+$ in the subject.

In another aspect, the present invention is a method for improving neuronal function and motor skills in a subject. The method comprises administering to the subject an effective amount of an agent that increases the level of NAD$^+$ in the subject.

In another aspect, the present invention is a method for preventing or treating neurotoxic damage in a subject. The method comprises administering to a subject who has undergone psychological or physical stress, exposure to toxic chemicals, radiation, shock, explosive shock, electrocution, mechanical injury, surgical injury, thermal injury, exhaustion, hypoxia, anoxia, blood loss, stroke, inflammation, auto-inflammation, infection, wound healing, malnutrition, drug addiction, drug overdose, or other injuries, or will be exposed to said stresses, an effective amount of an agent that increases the level of NAD$^+$ in the subject, whereby neurotoxic damage is prevented.

We disclose herein that raising NAD$^+$ levels improves cognitive performance and prevents neurocognitive decline.

We disclose herein that raising NAD$^+$ levels treats pain, and increases resistance to pain.

We disclose herein that raising NAD$^+$ levels increases voluntary activity, endurance and stamina.

In a first aspect, the disclosure encompasses a method for preventing toxicity and damage to neural tissues during disease, psychological stress, physical stress, exposure to toxic chemicals, radiation, shock, explosive shock, electrocution, mechanical injury, surgical injury, thermal injury, exhaustion, hypoxia, anoxia, blood loss, stroke, malnutrition, drug addiction, drug overdose, wound healing, inflammation, infection, exposure to pollution such as air and water pollution, or other injuries.

In some embodiments, the neurotoxic damage prevented is damage that causes neurocognitive impairment.

In some embodiments, the neurotoxic damage prevented is damage that causes pain and/or peripheral neuropathies.

In some embodiments, the neurotoxic damage prevented is damage that causes physical inactivity, lethargy or malaise.

In some embodiments, the neurotoxic damage prevented is damage that causes depression, anxiety, post-traumatic stress disorder, impaired sleep or other circadian rhythm disorders, impaired mental health or other neuropsychological disorders.

In another aspect, the disclosure encompasses a method for treating pain, and providing resistance to increased pain.

We disclose herein that raising NAD$^+$ levels provides robust protection against chemotherapy-induced toxicity to healthy neural tissues, and can prevent or treat chemotherapy and/or radiotherapy-induced peripheral neuropathies (CIPN), chemotherapy and/or radiotherapy-induced cognitive impairments (CICI), and chemotherapy and/or radiotherapy induced inactivity, lethargy, malaise, anxiety, depression, impaired sleep or other circadian rhythm disorders, impaired mental health or other neuropsychological disorders.

In another aspect, the disclosure encompasses a method for preventing chemotherapy- and/or radiotherapy induced neurotoxic damage in a subject. The method includes the step of administering to a subject who has undergone chemotherapy, is undergoing chemotherapy and/or radiotherapy, or will undergo chemotherapy and/or radiotherapy an effective amount of an agent that increases the level of NAD$^+$ in the subject, whereby chemotherapy-induced neurotoxic damage is prevented.

In some embodiments, the chemotherapy and/or radiotherapy-induced neurotoxic damage prevented is damage that is associated with chemotherapy-induced cognitive impairments (CICI).

In some embodiments, the chemotherapy and/or radiotherapy-induced neurotoxic damage prevented is damage that is associated with chemotherapy and/or radiotherapy-induced peripheral neuropathies (CIPN).

In some embodiments, the chemotherapy and/or radiotherapy induced damage prevented is damage that is associated with chemotherapy and/or radiotherapy induced inactivity, lethargy or malaise.

In some embodiments, the chemotherapy and/or radiotherapy induced damage prevented is damage that is associated with chemotherapy and/or radiotherapy induced depression, anxiety, impaired sleep, circadian rhythm disorders, impaired mental health, or other neurophychological or neuropsychiatric disorders.

In some embodiments, the agent is administered before, at the same time as, or after a chemotherapy agent is administered to the subject. In some such embodiments, the chemotherapy agent is selected from a group consisting of cisplatin, carboplatin, oxaliplatin, cyclophosphamide, altretamine, plicamydin, chlorambucil, chlormethine, ifosfamide, melphalan, carmustine, fotemustine, lomustine, streptozocin, busulfan, dacarbazine, mechlorethamine, procarbazine, temozolomide, thioTEPA, uramustine, paclitaxel, docetaxel, vinblastine, vincristine, vindesine, vinorelbine, hexamethylmelamine, etoposide, teniposide, methotrexate, pemetrexed, raltitrexed, cladribine, clofarabine, fludarabine, mercaptopurine, tioguanine, capecitabine, cytarabine, fluorouracil, fluxuridine, gemcitabine, daunorubicin, doxorubicin, epirubicin, idarubicin, mitoxantrone, valrubicin, bleomycin, hydroxyurea, mitomycin, topotecan, irinotecan, aminolevulinic acid, methyl aminolevulinate, porfimer sodium, verteporfin, alitretinoin, altretamine, amsacrine, anagrelide, arsenic trioxide, asparaginase, bexarotene, bortezomib, celecoxib, denileukin, diftitox, erlotinib, estramustine, gefitinib, hydroxycarbamide, imatinib, pentostatin, masoprocol, mitotane, pegaspargase, tretinoin, and combinations thereof.

In some embodiments, the agent is administered before, at the same time as, or after radiotherapy.

In some embodiments, the agent that increases the level of NAD$^+$ is an NAD$^+$ precursor. In some such embodiments, the NAD$^+$ precursor is selected from the group consisting of nicotinamide mononucleotide (NMN), nicotinic acid, nicotinamide, nicotinamide riboside (NR), nicotinic acid mononucleotide, nicotinic acid riboside, AICAR, adenosine, adenine, adenosine monophosphate, an analog, hetero- or homo-dimer, oligomer or polymer of any of the foregoing, or a salt or prodrug thereof.

In some embodiments, the agent that increases the level of NAD$^+$ is administered at a dose of between 0.5-5 grams per day.

In some embodiments, the agent that increases the level of NAD$^+$ is selected from the group consisting of an enzyme involved in NAD$^+$ biosynthesis, an enzymatically active fragment of such an enzyme, a nucleic acid encoding for an enzyme involved in NAD$^+$ biosynthesis, and an enzymatically active fragment of such a nucleic acid. In some such embodiments, the enzyme is NMNAT-1, NMNAT2, NMNAT3 or NAMPT.

In some embodiments, the agent that increases the level of NAD$^+$ is an activator to an enzyme involved in NAD$^+$ biosynthesis.

In some embodiments, the agent that increases the level of NAD$^+$ is an inhibitor of an NAD$^+$ consuming enzyme such as CD38 or PARP. In one embodiment, the agent may include apigenin, luteolin, tryphostin 8, as well as some compounds developed by GSK: thiozoloquin(az)olin(on)es. See Haffner C D et al J Med Chem 2015.

In some embodiments, the subject is a human.

In another aspect, the disclosure encompasses an agent that increases the level of NAD$^+$ for use in preventing chemotherapy and/or radiotherapy-induced neurotoxic damage in a subject.

In one aspect, the present invention is an agent that increases the level of NAD$^+$ for use in preventing neurotoxic injury.

In another aspect, the present invention is an agent that increases the level of NAD$^+$ for use in preventing neurocognitive and neuropathic decline.

In another aspect, the present invention is an agent that increases the level of NAD$^+$ for use in preventing or treating pain, neuropathies and associated disorders; and providing increased resistance to pain, neuropathies and associated disorders.

In another aspect, the present invention is an agent that increases the level of NAD$^+$ for use in increasing cognitive performance.

In another aspect, the present invention is an agent that increases the level of NAD$^+$ for use in increasing voluntary activity, endurance, and stamina.

In another aspect, the present invention is an agent that increases the level of NAD$^+$ for use in preventing cramps, tremors, spasms, paralysis, neuromuscular paralysis, hearing loss, vision impairment, taste loss, improving or preventing decline in skills, gait, and co-ordination.

In another aspect, the present invention is an agent that increases the level of NAD$^+$ for use in preventing or treating sexual dysfunction associated with nerve damage or impairment.

In another aspect, the present invention is an agent that increases the level of NAD$^+$ for use in improving neuronal function and motor skills.

In some embodiments, the chemotherapy and/or radiotherapy-induced neurotoxic damage prevented is damage that is associated with chemotherapy and/or radiotherapy-induced cognitive impairments (CICI).

In some embodiments, the chemotherapy and/or radiotherapy-induced neurotoxic damage prevented is damage that is associated with chemotherapy-induced peripheral neuropathies (CIPN).

In some embodiments, the chemotherapy and/or radiotherapy induced neurotoxic damage prevented is damage that is associated with chemotherapy and/or radiotherapy-induced inactivity, lethargy or malaise.

In some embodiments, the chemotherapy and/or radiotherapy induced neurotoxic damage prevented is damage that is associated with chemotherapy and/or radiotherapy-induced depression, anxiety, impaired sleep, circadian rhythm disorder, or other psychological disorder.

In some embodiments, the agent is an NAD$^+$ precursor. In some such embodiments, the NAD$^+$ precursor is selected from the group consisting of nicotinamide mononucleotide (NMN), nicotinic acid, nicotinamide, nicotinamide riboside (NR), nicotinic acid mononucleotide, nicotinic acid riboside, AICAR, adenosine, adenine, adenosine monophosphate, an analog, hetero- or homo-dimer, oligomer or polymer of any of the foregoing, or a salt or prodrug thereof.

In some embodiments, the agent that raises NAD$^+$ is an inhibitor of an NAD+ consuming enzyme, such as CD38 or a PARP enzyme.

In some embodiments, the agent is selected from the group consisting of an enzyme involved in NAD$^+$ biosynthesis, an enzymatically active fragment of such an enzyme, a nucleic acid encoding for an enzyme involved in NAD$^+$ biosynthesis, and an enzymatically active fragment of such a nucleic acid. In some such embodiments, the enzyme is NMNAT-1, NMNAT2, NMNAT3 or NAMPT.

In some embodiments, the agent that increases the level of NAD$^+$ is an activator to an enzyme involved in NAD$^+$ biosynthesis.

In some embodiments, the present invention is an agent that increases the level of NAD$^+$ for use in manufacturing a medicament for preventing neural damage or decline.

In some embodiments, the present invention is an agent that increases the level of NAD$^+$ for use in manufacturing a medicament for improving neural function, including improved neurocognitive function.

In another aspect, the disclosure encompasses an agent that increases the level of NAD$^+$ for use in manufacturing a medicament for preventing chemotherapy and/or radiotherapy-induced neurotoxic damage in a subject.

In some embodiments, the chemotherapy and/or radiotherapy-induced neurotoxic damage prevented is damage that is associated with chemotherapy and/or radiotherapy-induced cognitive impairments (CICI).

In some embodiments, the chemotherapy and/or radiotherapy-induced neurotoxic damage prevented is damage that is associated with chemotherapy-induced peripheral neuropathies (CIPN).

In some embodiments, the agent that increases the level of NAD$^+$ is an NAD$^+$ precursor. In some such embodiments, the NAD$^+$ precursor is selected from the group consisting of nicotinamide mononucleotide (NMN), nicotinic acid, nicotinamide, nicotinamide riboside (NR), nicotinic acid mononucleotide, nicotinic acid riboside, AICAR, adenosine, adenine, adenosine monophosphate, an analog, hetero- or homo-dimer, oligomer or polymer of any of the foregoing, or a salt or prodrug thereof.

In some embodiments, the agent is selected from the group consisting of an enzyme involved in $NAD^+$ biosynthesis, an enzymatically active fragment of such an enzyme, a nucleic acid encoding for an enzyme involved in $NAD^+$ biosynthesis, and an enzymatically active fragment of such a nucleic acid. In some such embodiments, the enzyme is NMNAT-1, NMNAT2, NMNAT3 or NAMPT.

In some embodiments, the agent is an activator to an enzyme involved in $NAD^+$ biosynthesis.

In another aspect, the present invention is a method for treating neurotoxic damage, neuropathy or improving neural function in a subject. The method comprises administering to a subject in need thereof an effective amount of an agent that increases the level of $NAD^+$ in the subject, whereby one of the symptoms of neurotoxic damage is decreased.

In one embodiment, the neurotoxic damage treated is damage that is associated with cognitive impairment.

In one embodiment, the neurotoxic damage treated is damage that is associated with peripheral neuropathy and/or pain.

In one embodiment, the neurotoxic damage treated is damage that is associated with inactivity, lethargy and malaise.

In one embodiment, the neurotoxic damage treated is damage that is associated with depression, anxiety, post-traumatic stress disorder, impaired sleep, circadian rhythm disruption, and other neuropsychological disorders.

In another aspect, the disclosure encompasses a method for treating chemotherapy and/or radiotherapy-induced neurotoxic damage in a subject. The method includes the step of administering to a subject in need thereof an effective amount of an agent that increases the level of $NAD^+$ in the subject, whereby one or more symptoms of chemotherapy-induced neurotoxic damage is decreased.

In some embodiments, the chemotherapy and/or radiotherapy-induced neurotoxic damage treated is damage that is associated with chemotherapy-induced cognitive impairments (CICI).

In some embodiments, the chemotherapy and/or radiotherapy-induced neurotoxic damage treated is damage that is associated with chemotherapy-induced peripheral neuropathies (CIPN).

In some embodiments, the one or more symptoms of chemotherapy and/or radiotherapy-induced neurotoxic damage may include, without limitation, a burning sensation, a tingling sensation, loss of feeling, difficulty using fingers to pick up or hold objects, dropping objects, difficulties with balance, tripping or stumbling while walking, or pressure or temperature sensitivity.

In one embodiment, the chemotherapy and/or radiotherapy-induced neurotoxic treated is damage that is associated with inactivity, lethargy and malaise.

In one embodiment, the chemotherapy and/or radiotherapy-induced neurotoxic treated is damage that is associated with depression, anxiety, impaired sleep, circadian rhythm disturbance, and other mental health or neuropsychological disorders.

In some embodiments, the $NAD^+$ raising agent is given in conjunction with existing pain therapies, such as paracetamol, aspirin, ibuprofen, opioids, to improve efficacy, decrease the required dose of co-administered pain therapies, or replace some agents in existing pain therapy combinations, or providing increased resistance to pain.

In some embodiments, the agent that increases the level of $NAD^+$ is an $NAD^+$ precursor. In some such embodiments, the $NAD^+$ precursor is selected from the group consisting of nicotinamide mononucleotide (NMN), nicotinic acid, nicotinamide, nicotinamide riboside (NR), nicotinic acid mononucleotide, nicotinic acid riboside, AICAR, adenosine, adenine, adenosine monophosphate, an analog, hetero- or homo-dimer, oligomer or polymer of any of the foregoing, or a salt or prodrug thereof.

In some embodiments, the agent that increases the level of $NAD^+$ is an inhibitor of an $NAD^+$ consuming enzyme, such as CD38 or PARP.

In some embodiments, the agent that increases the level of $NAD^+$ is administered at a dose of between 0.5-5 grams per day. In some embodiments, the agent that increases the level of $NAD^+$ is selected from the group consisting of an enzyme involved in $NAD^+$ biosynthesis, an enzymatically active fragment of such an enzyme, a nucleic acid encoding for an enzyme involved in $NAD^+$ biosynthesis, and an enzymatically active fragment of such a nucleic acid. In some such embodiments, the enzyme is NMNAT-1, NMNAT2, NMNAT3 or NAMPT.

In some embodiments, the agent that increases the level of $NAD^+$ is an activator to an enzyme involved in $NAD^+$ biosynthesis.

In one embodiment, the subject is a mammal selected from the group consisting of a racehorse, a companion pet and a livestock.

In some embodiments, the subject is a human.

In another aspect, the present invention is an agent that increases the level of $NAD^+$ for use in treating neural damage in a subject.

In one embodiment, the neural damage treated or prevented is damage that is associated with cognitive impairment.

In one embodiment, the neural damage treated or prevented is damage that is associated with peripheral neuropathy and/or pain.

In one embodiment, the neural damage treated or prevented is damage that is associated with inactivity, lethargy and malaise.

In one embodiment, the neural damage treated or prevented is damage that is associated with depression, anxiety, impaired sleep, circadian rhythm disturbances, impaired mental health, and other neuropsychological disorders.

In one embodiment, the neural damage treated or prevented is damage that is associated with psychological or emotional stress and associated disorders, such as post-traumatic stress disorder.

In another aspect, the present invention is an agent that increases the level of $NAD^+$ for use in preventing, treating pain and/or increasing resistance to pain.

In another aspect, the present invention is an agent that increases the level of $NAD^+$ for use in improving neural function in a subject, to enhance cognitive performance, motor skills, voluntary activity, stamina and endurance, and provide resistance to pain and neuropathy.

In another aspect, the disclosure encompasses an agent that increases the level of $NAD^+$ for use in treating chemotherapy and/or radiotherapy-induced neurotoxic damage in a subject.

In some embodiments, the chemotherapy and/or radiotherapy-induced neurotoxic damage treated is damage that is associated with chemotherapy and/or radiotherapy-induced cognitive impairments (CICI).

In some embodiments, the chemotherapy and/or radiotherapy-induced neurotoxic damage prevented is damage that is associated with chemotherapy and/or radiotherapy-induced peripheral neuropathies (CIPN).

In one embodiment, the chemotherapy and/or radiotherapy-induced neurotoxic damage prevented is inactivity, lethargy and malaise.

In one embodiment, the chemotherapy and/or radiotherapy-induced neurotoxic damage prevented is depression, anxiety, impaired sleep, impaired circadian rhythm, mental health disorders and other neuropsychological disorders.

In some embodiments, the agent is an $NAD^+$ precursor. In some such embodiments, the $NAD^+$ precursor is selected from the group consisting of nicotinamide mononucleotide (NMN), nicotinic acid, nicotinamide, nicotinamide riboside (NR), nicotinic acid mononucleotide, nicotinic acid riboside, AICAR, adenosine, adenine, adenosine monophosphate, an analog, hetero- or homo-dimer, oligomer or polymer of any of the foregoing, or a salt or prodrug thereof.

In some embodiments, the agent is selected from the group consisting of an enzyme involved in $NAD^+$ biosynthesis, an enzymatically active fragment of such an enzyme, a nucleic acid encoding for an enzyme involved in $NAD^+$ biosynthesis, and an enzymatically active fragment of such a nucleic acid. In some such embodiments, the enzyme is NMNAT-1, NMNAT2, NMNAT3 or NAMPT.

In some embodiments, the agent is an activator to an enzyme involved in $NAD^+$ biosynthesis.

In another aspect, the disclosure encompasses an agent that increases the level of $NAD^+$ for use in manufacturing a medicament for treating chemotherapy and/or radiotherapy-induced neurotoxic damage in a subject.

In some embodiments, the chemotherapy and/or radiotherapy-induced neurotoxic damage treated is damage that is associated with chemotherapy and/or radiotherapy-induced cognitive impairments (CICI).

In some embodiments, the chemotherapy and/or radiotherapy-induced neurotoxic damage prevented is damage that is associated with chemotherapy and/or radiotherapy-induced peripheral neuropathies (CIPN).

In some embodiments, the agent is an $NAD^+$ precursor. In some such embodiments, the $NAD^+$ precursor is selected from the group consisting of nicotinamide mononucleotide (NMN), nicotinic acid, nicotinamide, nicotinamide riboside (NR), nicotinic acid mononucleotide, nicotinic acid riboside, AICAR, adenosine, adenine, adenosine monophosphate, an analog, hetero- or homo-dimer, oligomer or polymer of any of the foregoing, or a salt or prodrug thereof.

In some embodiments, the agent is selected from the group consisting of an enzyme involved in $NAD^+$ biosynthesis, an enzymatically active fragment of such an enzyme, a nucleic acid encoding for an enzyme involved in $NAD^+$ biosynthesis, and an enzymatically active fragment of such a nucleic acid. In some such embodiments, the enzyme is NMNAT-1, NMNAT2, NMNAT3 or NAMPT.

In some embodiments, the agent is an activator to an enzyme involved in $NAD^+$ biosynthesis.

In another embodiment, the agent is used to prevent, treat or increase resistance to pain and neuropathies. Non-limiting examples of this include chemical exposure, radiation exposure, light exposure, wounds, trauma, mechanical stress, thermal stress, high temperatures, low temperatures, sunburn, neuropathic diseases, or diseases that result in damage to nerves.

In another embodiment, the agent is administered in combination with or in place of painkillers, such as paracetamol, aspirin, ibuprofen, or opioids. Co-administration with the agent as disclosed here may be used to lower the necessary dose of painkillers, and/or improve efficacy, or replace the need for certain painkillers.

In another embodiment, the agent is used to treat neurological disorders that result in memory loss or impaired cognitive functions, such as Alzheimer's disease, dementia, or Parkinson's disease.

In another aspect, the present invention is an agent that increases $NAD^+$ for improving pain tolerance.

In another aspect, the present invention is an agent that increases $NAD^+$ for treating phantom limbs.

In another aspect, the present invention is an agent that increases $NAD^+$ delivered prior to, at the same time as, in combination with, after treatment with, or in place of pain therapies such as ibuprofen, aspirin, paracetamol, opioids, and other pain therapies, for the treatment of pain.

In another aspect, the present invention is an agent that increases NAD+ delivered prior to, at the same time as, in combination with, after treatment with, or in place of anti-inflammatory therapies, including without limitation corticosteroids selected from the group consisting of dexamethasone and methylprednisolone and non-steroidal anti-inflammatory agents selected from the group consisting of ibuprofen, aspirin, indomethacin, COX-2 inhibitors, and mefenamic acid for the treatment of pain and neuropathies.

In another aspect, the present invention is an agent that increases $NAD^+$ for increasing voluntary physical activity, stamina and endurance.

In another aspect, the present invention is an agent that increases $NAD^+$ for improving cognitive performance.

In another aspect, the present invention is an agent that increases $NAD^+$ for treating or protecting against depression, anxiety, post-traumatic stress disorder, substance abuse, and other mental health or neuropsychological disorders.

In another aspect, the present invention is an agent that increases $NAD^+$ for preventing or treating diabetic neuropathy.

In another aspect, the present invention is an agent that increases $NAD^+$ for preventing or treating substance abuse and addiction.

In another aspect, the present invention is an agent that increases $NAD^+$ for preventing neurocognitive or neurodevelopmental disorders caused by exposure to pollution including air pollution, water pollution, and food contamination.

In another aspect, the present invention is an agent that prevents or treats nerve and neuron damage.

In one embodiment, the $NAD^+$ precursor is selected from the group consisting of nicotinamide mononucleotide (NMN), nicotinic acid, nicotinamide, nicotinamide riboside (NR), nicotinic acid mononucleotide, nicotinic acid riboside, AICAR, adenosine, adenine, adenosine monophosphate, an analog, hetero- or homo-dimer, oligomer or polymer of any of the foregoing, or a salt or prodrug thereof.

In one embodiment, the agent is selected from the group consisting of an enzyme involved in $NAD^+$ biosynthesis, an enzymatically active fragment of such an enzyme, a nucleic acid encoding for an enzyme involved in $NAD^+$ biosynthesis, and an enzymatically active fragment of such a nucleic acid.

In one embodiment, the enzyme is NMNAT-1, NMNAT2, NMNAT3 or NAMPT.

In one embodiment, the agent is an activator to an enzyme involved in $NAD^+$ biosynthesis.

BRIEF DESCRIPTION OF THE DRAWINGS

FIGS. 1A-1D. Male SD rats were subjected to baseline testing prior to addition of NMN to drinking water (500 mg/L) 24 prior and 24 hr subsequent to a single i.p. injection of doxorubicin (4 mg/kg) with or without co-administration of NMN (200 mg/kg). A) Voluntary wheel running, followed by B) the von Frey test for mechanical allodynia (pain) at day 3. At day 8, C) short term spatial memory was assessed using the novel location recognition test. At day 9, D) short term object memory was assessed using the novel object recognition test. n=8, *p<0.05, p<0.01, **p<0.0001. Dunn's multiple comparison test, Kruskal Wallis one-way ANOVA.

Figures 2A, 2B:
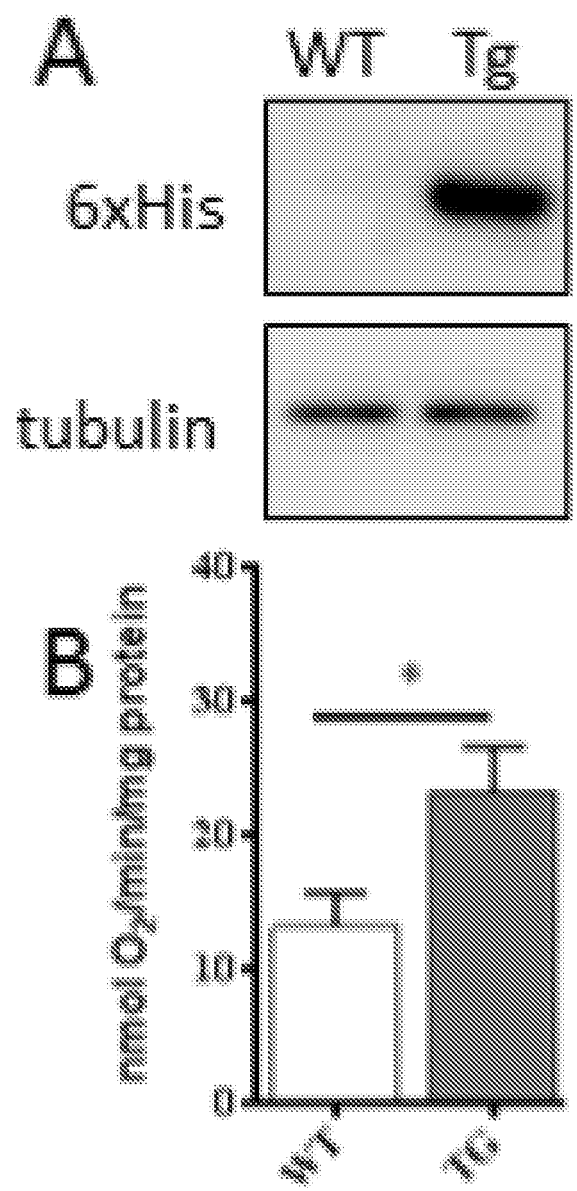

FIGS. 2A-2B. A) His-tag western blot for expression of NMNAT3-His transgene in brain. B) Palmitoyl-carnitine mitochondrial respiration in tissue (liver) of NMNAT3 transgenics.

Figures 3A, 3B, 3C:
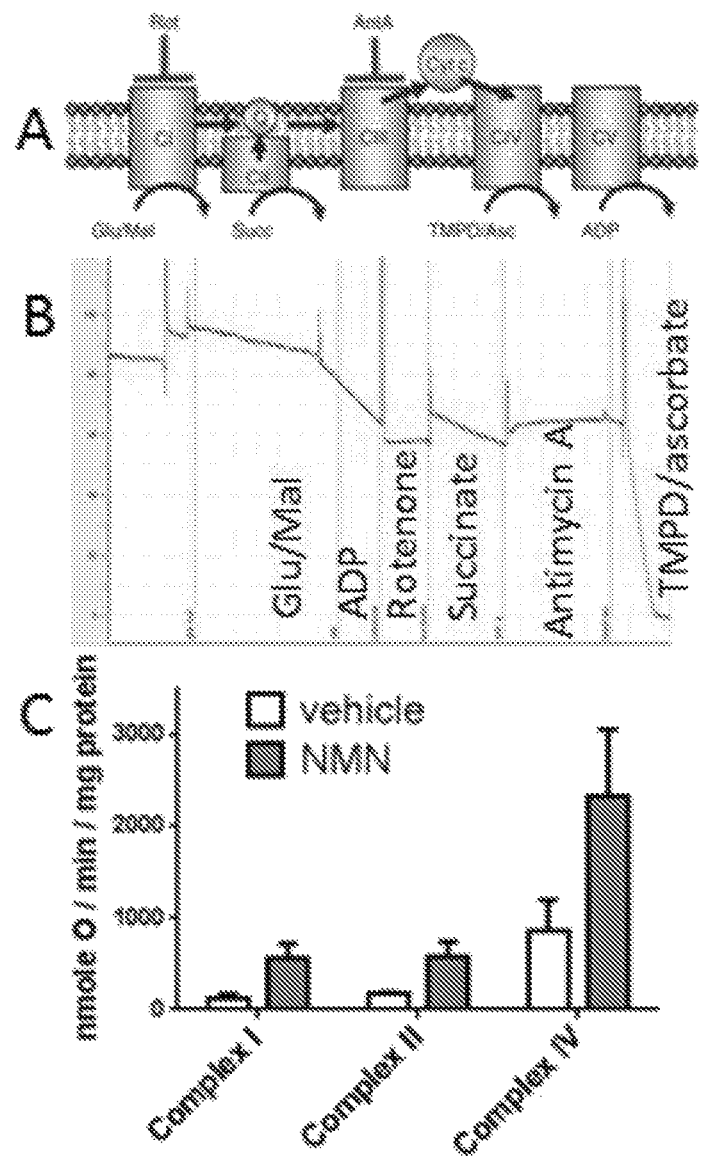

FIGS. 3A-3C. A) Experimental design for probing mitochondrial respiration [43], B) example trace of O2 consumption rates in a Clarke type electrode, C) changes in respiratory capacity of muscle mitochondria of aged NMN treated mice.

DETAILED DESCRIPTION

I. Definitions

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The terms "optional" or "optionally" as used herein means that a subsequently described event or circumstance may but need not occur, and that the description includes instances where the event or circumstance occurs and instances in which it does not. For example, "optional bond" means that the bond may or may not be present, and that the description includes single, double, or triple bonds.

The term "neuropathies" as used herein refers to any disease or condition involving neurons and/or supporting cells, such as for example, glia, muscle cells, fibroblasts, etc., and, in particular, those diseases or conditions involving axonal damage. Axonal damage can be caused by traumatic injury, by non-mechanical injury due to diseases or conditions, or by chemically induced injury or damage. The result of such damage can be degeneration or dysfunction of the axon and loss of functional neuronal activity. Disease and conditions producing or associated with such axonal damage are among a large number of neuropathic diseases and conditions. Such neuropathies can include peripheral neuropathies, central neuropathies, and combinations thereof. Furthermore, peripheral neuropathic manifestations can be produced by diseases focused primarily in the central nervous systems and central nervous system manifestations can be produced by essentially peripheral or systemic diseases.

The term "chemotherapy-induced peripheral neuropathy" or "CIPN" as used herein refers to a progressive, enduring, and often irreversible condition featuring pain, numbness, tingling and sensitivity to cold in the hands and feet (sometimes progressing to the arms and legs), and esophagus, that afflicts between 30 and 40 percent of patients undergoing chemotherapy. In CIPN, an anticancer drug could impair both sensory and motor functions. The symptoms usually start in the hands and/or feet and creep up the arms and legs. Sometimes it feels like a tingling or numbness. Other times, it's more of a shooting and/or burning pain or sensitivity to temperature. It can include sharp, stabbing pain. CIPN can also lead to hearing loss, blurred vision and change in taste. CIPN can make it difficult to perform normal day-to-day tasks like buttoning a shirt, sorting coins in a purse, or walking. In addition, the motor neuron dysfunction manifest as cramps, difficulty with fine motor activities (e.g. writing or dialing a phone), gait disturbances, paralysis, spasms, tremors and weakness. Similar disturbances are observed during radiotherapy.

Chemotherapeutic agents are commonly grouped according to their mode of action and/or the cellular target upon which they act. For example, chemotherapeutic agents may categorized as DNA-interactive agents (including. topoisomerase inhibitors, DNA strand breakage agents and DNA minor groove binders), alkylating agents, antimetabolites, tubulin-interactive agents and hormonal agents. Chemotherapeutic agents to which methods of the present application are applicable may be selected from any of these exemplary groups, but are not limited thereto. For a detailed discussion of chemotherapeutic agents and their method of administration, see Dorr, et al, Cancer Chemotherapy Handbook, 2d edition, pages 15-34, Appleton and Lang (Connecticut, 1994) herein incorporated by reference.

Chemotherapy drugs or agents associated with CIPN include, but not limited to, arsenic trioxide (Trisenox), cytarabine (Cytosar-U, Depocyt, generics), etoposide, hexamethylmelamine (altretamine [Hexalen]), Ifosfamide (Ifex, generics), methotrexate (Trexall, generics), procarbazine (Matulane) and vinblastine, thalidomide, the epothilones such as Ixabepilone (Ixempra Kit), the *vinca* alkaloids vincristine and vinblastine, the taxanes paclitaxel and docetaxel, epothilones (ixabepilone), thalidomide (Thalomid), lenalidomide, the proteasome inhibitors such as bortezomib (Velcade), and the platinum-based drugs cisplatin, oxaliplatin and carboplatin.

By way of example only, according to methods of the invention, chemotherapeutic agents may be selected from cisplatin, carboplatin, oxaliplatin, cyclophosphamide, altretamine, plicamydin, chlorambucil, chlormethine, ifosfamide, melphalan, carmustine, fotemustine, lomustine, streptozocin, busulfan, dacarbazine, mechlorethamine, procarbazine, temozolomide, thioTEPA, uramustine, paclitaxel, docetaxel, vinblastine, vincristine, vindesine, vinorelbine, hexamethylmelamine, etoposide, teniposide, methotrexate, pemetrexed, raltitrexed, cladribine, clofarabine, fludarabine, mercaptopurine, tioguanine, capecitabine, cytarabine, fluorouracil, fluxuridine, gemcitabine, daunorubicin, doxorubicin, epirubicin, idarubicin, mitoxantrone, valrubicin, bleomycin, hydroxyurea, mitomycin, topotecan, irinotecan, aminolevulinic acid, methyl aminolevulinate, porfimer sodium, verteporfin, alitretinoin, altretamine, amsacrine, anagrelide, arsenic trioxide, asparaginase, bexarotene, bortezomib, celecoxib, denileukin, diftitox, erlotinib, estramustine, gefitinib, hydroxycarbamide, imatinib, pentostatin, masoprocol, mitotane, pegaspargase, and tretinoin.

Whether CIPN arises, and to what degree, is determined by the choice of drug and/or radiotherapy, duration of use, the total amount consumed and whether the patient already has peripheral neuropathy. Though the symptoms are mainly sensory—pain, tingling, numbness, cramps, neuromuscular paralysis and temperature sensitivity—in some cases motor nerves are affected, and occasionally, also, the autonomic nervous system.

CIPN often follows the first chemotherapy dose and increases in severity as treatment continues, but this progression usually levels off at completion of treatment. The platinum-based drugs are the exception; with these drugs, sensation may continue to deteriorate for several months after the end of treatment and CIPN may persist for decades following treatment. Some CIPN appears to be irreversible.

Pain can often be helped with drug or other treatment but the numbness is usually resistant to treatment.

One of the mainstays of CIPN management is opioid based drug therapy. Opioid therapy presents clinical challenges such as opioid addiction, withdrawal symptoms, respiratory depression, constipation, dizziness, nausea, vomiting, constipation, and physical dependence. In addition, prescription of opioid therapies presents opportunities for abuse and criminal activity. Alternatives to opioid based therapies would be preferable from a medical perspective, psychological perspective and from a law enforcement perspective.

CIPN disrupts leisure, work and family relations, and the pain of CIPN is often accompanied by sleep and mood disturbance, fatigue and functional difficulties. A 2007 American study found that most patients did not recall being told to expect CIPN, and doctors monitoring the condition rarely asked how it affects daily living but focused on practical effects such as dexterity and gait. It is not known what causes the condition, but microtubule and mitochondrial damage, and leaky blood vessels near nerve cells are some of the possibilities being explored.

The terms "chemotherapy-induced cognitive dysfunction or impairment," "CICI," "post-chemotherapy cognitive impairment," or "PCCI" as used herein refer to the cognitive impairment that can result from chemotherapy treatment. Approximately 20-30% of people who undergo chemotherapy experience some level of post-chemotherapy cognitive impairment.

CICI may seriously affect quality of life and life itself in cancer patients. CICI may manifest in many ways, including encephalopathy syndromes and confusional states, seizure activity, headache, cerebrovascular complications and stroke, visual loss, cerebellar dysfunction, and spinal cord damage with myelopathy. It is now known that, as a result of treatment, a subset of cancer survivors experience cognitive problems that can last for many years after the completion of chemotherapy. The cognitive problems include attention deficits, memory loss, and confused thought processes. Up to 70% of patients report that their cognitive difficulties persist well beyond the duration of treatment.

The etiology of chemotherapy and/or radiotherapy-induced cognitive impairment is largely unknown, but several candidate mechanisms have been suggested, including oxidative stress, impaired blood-brain barrier (BBB), neuroinflammation, decreased neurogenesis, etc.

As used herein the terms "treating", "treatment", "preventing" and "prevention" refer to any and all uses which remedy a condition or symptoms, prevent the establishment of a condition or disease, or otherwise prevent, hinder, retard, or reverse the progression of a condition or disease or other undesirable symptoms in any way whatsoever. Thus the terms "treating" and "preventing" and the like are to be considered in their broadest context, For example, treatment does not necessarily imply that a patient is treated until total recovery. Similarly, in the present context, treatment also includes within its scope the reversal of existing nerve damage or neuropathy, but not necessarily the complete reversal thereof to normal levels that would be expected in the absence of such nerve damage or neuropathy having occurred.

The term "neuropathy-associated condition" as used herein refers to a condition associated with, at least in part, nerve damage, in particular to neurons of the peripheral nervous system. The condition may be characterized by such damage, may occur as a result, either directly or indirectly, of such damage or itself lead to such nerve damage. Typically a "neuropathy-associated condition" will share at least one symptom in common with neuropathy, typically peripheral neuropathy, Such symptoms include pain, loss of sensation, including numbness, tingling or burning sensations in limbs or body extremities, parasthesia, muscle weakness, a reduction in neuromuscular reflex, cramping, neuromuscular paralysis, and sexual dysfunction.

As used herein, the term "subject" means a human or non-human animal selected for treatment or therapy. The phrases "therapeutically-effective amount" and "effective amount" as used herein means the amount of an agent which is effective for producing the desired therapeutic effect in at least a sub-population of cells in a subject at a reasonable As used herein, the term "prodrug" means a derivative of a compound that can hydrolyze, oxidize, or otherwise react under biological conditions (in vitro or in vivo) to provide a compound described herein as useful in the methods of the invention. While prodrugs typically are designed to provide active compound upon reaction under biological conditions, prodrugs may have similar activity as a prodrug. The references by Goodman and Gilman (The Pharmacological Basis of Therapeutics, 8th Ed, McGraw-Hill, Int. Ed. 1992, "Biotransformation of Drugs", p 13-15); T. Higuchi and V. Stella (Pro-drugs as Novel Delivery Systems, Vol. 14 of the A.C.S. Symposium Series); and Bioreversible Carriers in Drug Design (E. B. Roche, ed., American Pharmaceutical Association and Pergamon Press, 1987) describing prodrugs generally are hereby incorporated by reference. Prodrugs of the compounds described herein can be prepared by modifying functional groups present in said component in such a way that the modifications are cleaved, either in routine manipulation or in vivo, to the parent component. Typical examples of prodrugs are described for instance in WO 99/33795, WO 99/33815, WO 99/33793 and WO 99/33792, each of which is incorporated herein by reference for these teachings. Prodrugs can be characterized by increased bio-availability and are readily metabolized into the active inhibitors in vivo.

Examples of prodrugs include, but are not limited to, analogs or derivatives of the compounds described herein, further comprising biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of the compounds described herein that comprise NO, N02, ONO, or ON02 moieties. Prodrugs are prepared using methods known to those of skill in the art, such as those described by BURGER'S MEDICINAL CHEMISTRY AND DRUG DISCOVERY (1995) 172-178, 949-982 (Manfred E. Wolff ed., 5th ed), the entire teachings of which are incorporated herein by reference.

As used herein, the term "salt" or "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio.

Pharmaceutically acceptable salts are well known in the art. For example, Berge et al., describes pharmaceutically acceptable salts in detail in J. Pharmaceutical Sciences (1977) 66: 1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N+(C1-4alkyl)$_4$ salts. Representative alkali or alkaline earth metal salts include sodium, lithium, potassium, calcium, magnesium, and the like. Further pharmaceutically acceptable salts include, when appropriate, non-toxic ammonium, quaternary ammonium, and amine cations formed using counterions such as halide, hydroxide, carboxylate, sulfate, phosphate, nitrate, lower alkyl sulfonate, and aryl sulfonate.

As used herein, the term "solvate" includes any combination which may be formed by a compound of this invention with a suitable inorganic solvent (e.g. hydrates) or organic solvent, such as but not limited to alcohols, ketones, esters and the like. Such salts, hydrates, solvates, etc. and the preparation thereof will be clear to the skilled person; reference is for instance made to the salts, hydrates, solvates, etc. described in U.S. Pat. Nos. 6,372,778, 6,369,086, 6,369,087 and 6,372,733.

As used herein, the term "NAD$^+$ precursor" refers to a precursor compound that is capable of incorporated into NAD$^+$ under physiological condition. Some exemplary NAD$^+$ precursors include, without limitation, tryptophan, quinolinic acid, nicotinic acid, nicotinamide, nicotinamide mononucleotide (NMN) nicotinamide riboside (NR), nicotinic acid mononucleotide, nicotinic acid riboside, AICAR, adenosine, adenine, adenosine monophosphate, and analogues, hetero- or homo-dimers, oligimers, polymers and prodrugs thereof.

As used herein, the term "increase NAD$^+$ level" refers to any means or method which can increase NAD$^+$ level in a subject. For example, one may increase NAD$^+$ level in a subject by administering to the subject an effective amount of an agent that increases the level of NAD$^+$ in the subject. Examples of such agents include any NAD$^+$ precursor as discussed above and as appreciated by one skilled in the art, such as NMN or a salt thereof or prodrug thereof. Other examples of agents may include an enzyme involved in NAD$^+$ biosynthesis, such as NMNAT-1 or NAMPT, or an enzymatically active fragment thereof, or a nucleic acid encoding an enzyme involved in NAD$^+$ biosynthesis, or an enzymatically active fragment thereof.

NAD$^+$ levels may be increased by increasing the activity of enzymes involved in NAD$^+$ biosynthesis (de novo synthesis or salvage pathways). Enzymes involved in NAD$^+$ biosynthesis such as nicotinate phosphoribosyl transferase 1 (NPT1), pyrazinamidase/nicotinamidase 1 (PNC1), nicotinic acid mononucleotide adenylyltransferase 1 (NMA1), nicotinic acid mononucleotide adenylyltransferase 2 (NMA2), nicotinamide N-methyltransferase (NNMT), nicotinamide phosphoribosyl transferase (NAMPT or NAMPRT), nicotinate/nicotinamide mononucleotide adenylyl transferase 1 (NMNAT-1), and nicotinamide mononucleotide adenylyl transferase 2 (NMNAT-2); are described in U.S. Pat. No. 7,977,049, which is incorporated by reference herein.

In one embodiment, NAD$^+$ levels in a subject may be increased administering to a subject an agent that increases the protein or activity level of the enzymes involved in NAD$^+$ biosynthesis as discussed above.

In certain embodiments, agents for such uses include soluble precursors to NAD$^+$ (e.g., tryptophan, quinolinic acid, nicotinamide mononucleotide, nicotinamide riboside, and nicotinic acid), fisetin, quercetin, resveratrol, DOI, hydroxytyrosol, pyrroloquinoline quinone, metformin, apigenin, luteolin, tryphostin 8, berberine, a CD38 inhibitor, SRT-1720, a SIRT1 activator, a compound of any one of fomiulas I-XV, or functional derivatives thereof.

The term "purified," as described herein, refers to the purity of a given compound. For example, a compound is "purified" when the given compound is a major component of the composition, i.e., at least 50% w/w pure. Thus, "purified" embraces at least 50% w/w purity, at least 60% w/w purity, at least 70% purity, at least 80% purity, at least 85% purity, at least 90% purity, at least 92% purity, at least 94% purity, at least 96% purity, at least 97% purity, at least 98% purity, at least 99% purity, at least 99.5% purity, and at least 99.9% purity, wherein "substantially pure" embraces at least 97% purity, at least 98% purity, at least 99% purity, at least 99.5% purity, and at least 99.9% purity.

The term "metabolite," as described herein, refers to a compound produced in vivo after administration to a subject in need thereof.

The term "about" means that the recited numerical value is part of a range that varies within standard experimental error.

The term "salts," as described herein, refers to a compound comprising a cation and an anion, which can produced by the protonation of a proton-accepting moiety and/or deprotonation of a proton-donating moiety. It should be noted that protonation of the proton-accepting moiety results in the formation of a cationic species in which the charge is balanced by the presence of a physiological anion, whereas deprotonation of the proton-donating moiety results in the formation of an anionic species in which the charge is balanced by the presence of a physiological cation.

The phrase "pharmaceutically acceptable salt" means a salt that is pharmaceutically acceptable. Examples of pharmaceutically acceptable salts include, but are not limited to: (1) acid addition salts, formed with inorganic acids such as hydrochloric acid, hydrobromic acid, sulfuric acid, nitric acid, phosphoric acid, and the like; or formed with organic acids such as glycolic acid, pyruvic acid, lactic acid, malonic acid, malic acid, maleic acid, fumaric acid, tartaric acid, citric acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, lauryl sulfuric acid, gluconic acid, glutamic acid, salicylic acid, muconic acid, and the like or (2) basic addition salts formed with the conjugate bases of any of the inorganic acids listed above, wherein the conjugate bases comprise a cationic component selected from among Na$^+$, K$^+$, Mg$^{2+}$, Ca$^{2+}$, NH$_g$R'''$^{4-g+}$, in which R''' is a C$_{1-3}$ alkyl and g is a number selected from among 0, 1, 2, 3, or 4. It should be understood that all references to pharmaceutically acceptable salts include solvent addition forms (solvates) or crystal forms (polymorphs) as defined herein, of the same acid addition salt.

The term "preparation" or "dosage form" is intended to include both solid and liquid formulations of the active compound and one skilled in the art will appreciate that an active ingredient can exist in different preparations depending on the desired dose and pharmacokinetic parameters.

The term "excipient" as used herein refers to a compound that is used to prepare a pharmaceutical composition, and is generally safe, non-toxic and neither biologically nor otherwise undesirable, and includes excipients that are acceptable for veterinary use as well as human pharmaceutical use.

"Nicotinamide," which corresponds to the following structure,

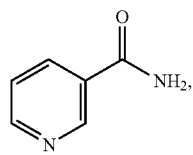

is one of the two principal forms of the B-complex vitamin niacin. The other principal form of niacin is nicotinic acid; nicotinamide, rather than nicotinic acid, however, is the major substrate for nicotinamide adenine dinucleotide (NAD) biosynthesis in mammals, as discussed in detail herein. Nicotinamide, in addition to being known as niacinamide, is also known as 3-pyridinecarboxamide, pyridine-3-carboxamide, nicotinic acid amide, vitamin B3, and vitamin PP. Nicotinamide has a molecular formula of $C_6H_6N_2O$ and its molecular weight is 122.13 Daltons. Nicotinamide is commercially available from a variety of sources.

"Nicotinamide Adenine Dinucleotide" (NAD), which corresponds to the following structure,

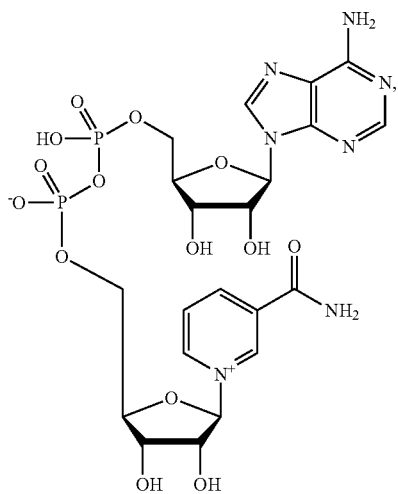

is produced from the conversion of nicotinamide to NMN, which is catalyzed by Nampt, and the subsequent conversion of NMN to NAD, which is catalyzed by Nmnat. Nicotinamide adenine dinucleotide (NAD) has a molecular formula of $C_{21}H_{27}N_7O_{14}P_2$ and a molecular weight of 663.43. Nicotinamide adenine dinucleotide (NAD) is commercially available from such sources as Sigma-Aldrich (St. Louis, Mo.). Nicotinamide adenine dinucleotide exists in two forms, an oxidized and reduced form abbreviated as NAD$^+$ and NADH respectively.

"Nicotinamide Mononucleotide" (NMN), which corresponds to the following structure,

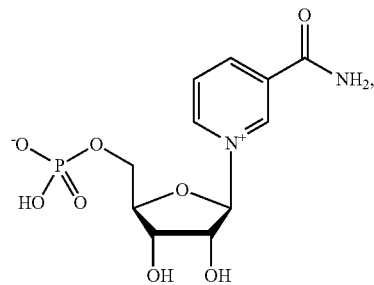

is produced from nicotinamide in the NAD biosynthesis pathway, a reaction that is catalyzed by Nampt. NMN is further converted to NAD in the NAD biosynthesis pathway, a reaction that is catalyzed by Nmnat. Nicotinamide mononucleotide (NMN) has a molecular formula of $C_{11}H_{15}N_2O_8P$ and a molecular weight of 334.22. Nicotinamide mononucleotide (NMN) is commercially available from such sources as Sigma-Aldrich (St. Louis, Mo.).

"Nicotinamide Riboside" (NR), which corresponds to the following structure,

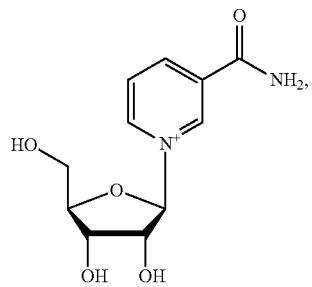

is characterized and a synthesized as described in, for instance, U.S. Pat. No. 8,106,184.

"Nicotinic Acid Mononuceotide" (NaMN) corresponds to the following structure:

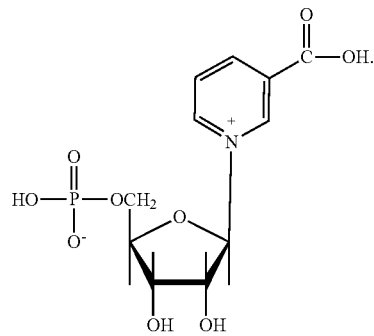

"Nicotinic Acid Riboside" (NaR) corresponds to the following structure:

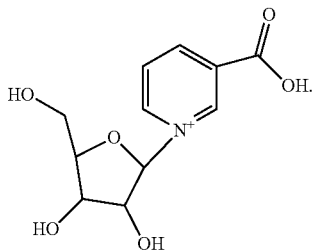 [SMILES: O=C(O)c1ccc[n+](C2OC(CO)C(O)C2O)c1]

"5-aminoimidazole-4-carboxamide ribonucleotode" (AICAR), which corresponds to the following structure,

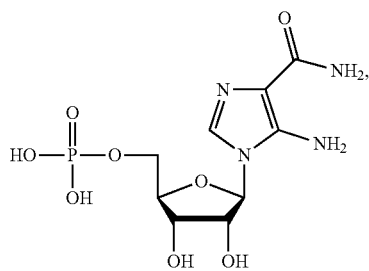

is a precursor of adenine dinucleotide (AMP).

II. Increasing $NAD^+$ Level Prevents Short and Long Term Chemotherapy and/or Radiotherapy Induced Peripheral Neuropathy and Cognitive Deficits During Chemotherapy Administration Chemotherapy and radiotherapy are crucial components of anticancer treatment and have led to dramatically increased survival rates in many cancers. While effective at killing cancer cells, a key, limiting factor in treatment is the fact that chemotherapeutic agents and radiotherapy have widespread toxicity to healthy tissues throughout the body, including the brain and nervous system. In the short term, this leads to painful neuropathies, fatigue, and neuropsychological impairments, all of which commonly extend to years after treatment. Preventing and treating neuropathies and neuropsychological impairments caused by chemotherapy and/or radiotherapy is therefore a critical goal in improving the quality of life of cancer patients, and improving their long term health outcomes.

Chemotherapy and/or radiotherapy induced loss of $NAD^+$ may lead to deranged gene expression, mitochondrial function, and reduced metabolic capacity which may underlie the neuropsychological disorders and neuropathic pain that results from cancer chemotherapy. This decline in NAD+ and subsequent metabolic and epigenetic dysfunction can be rescued by treatment with the cell permeable NAD+ precursor nicotinamide mononucleotide (NMN). Applicants' preliminary data shows that brief NMN treatment rescues neurocognitive deficiencies caused by the anthracycline chemotherapeutic doxorubicin, including impaired memory, decreased voluntary activity, and mechanical allodynia.

In one aspect, the present invention is a method for preventing or treating short and long term chemotherapy and/or radiotherapy induced peripheral neuropathy and cognitive deficits during chemotherapy administration by increasing $NAD^+$ level in a subject. Applicants found that increasing $NAD^+$ level in a subject can lead to preventing or treating short and long term chemotherapy induced peripheral neuropathy. By way of an example, Applicants demonstrate that administering a $NAD^+$ precursor (i.e., NMN) to increase $NAD^+$ level in a subject could lead to preventing or treating short and long term chemotherapy induced peripheral neuropathy.

In one embodiment, the method for preventing or treating chemotherapy and/or radiotherapy induced peripheral neuropathy and cognitive deficits in a subject in need thereof during chemotherapy and/or radiotherapy administration comprising the step of administering to the subject an effective amount of an agent that increases the level of $NAD^+$ in the subject.

Figures 1A, 1B, 1C, 1D:
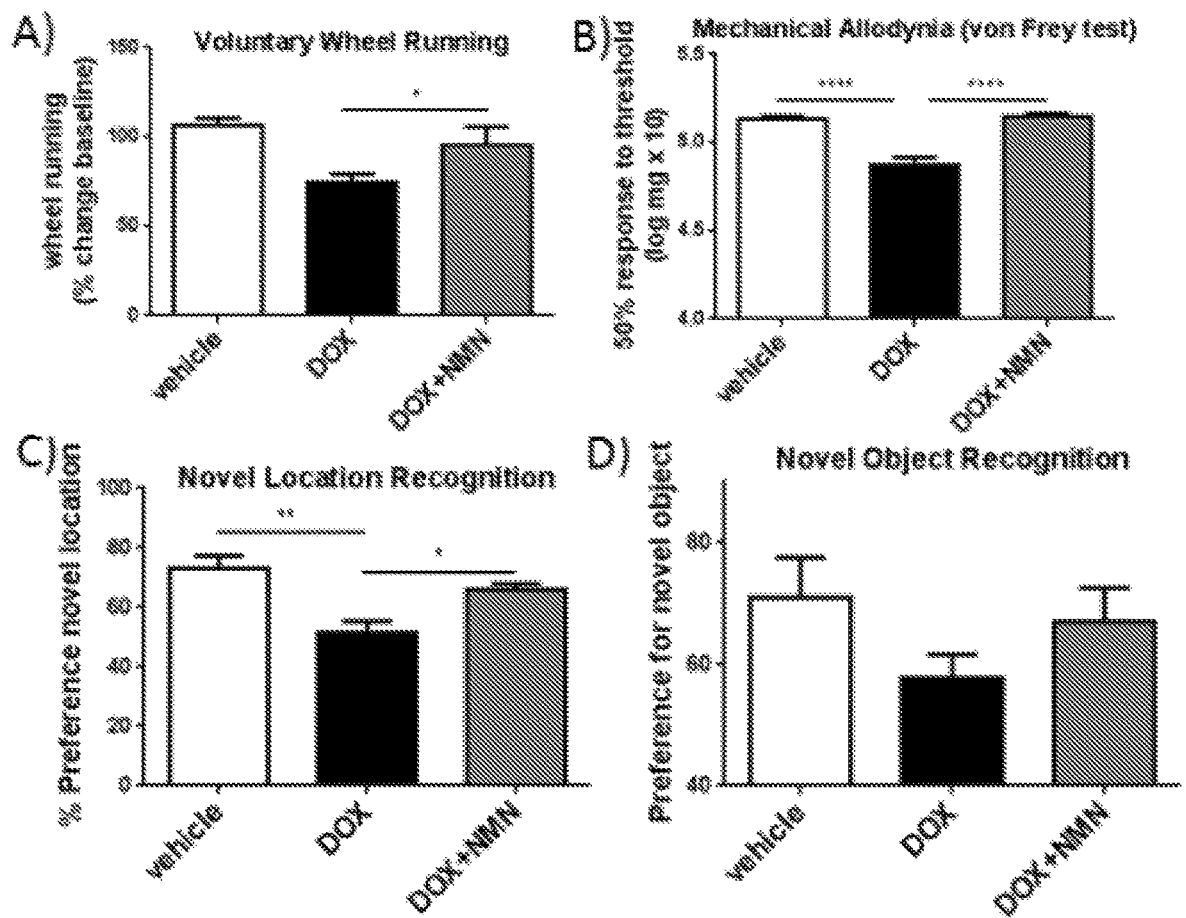

In one embodiment, the agent is an $NAD^+$ precursor. In one specific embodiment, the $NAD^+$ precursor is NMN or a salt thereof, or a prodrug thereof. Example 1 and FIG. 1 showed that NAD+ precursor NMN is effective in treating and preventing memory impairments, inactivity and allodynia caused by doxorubicin. As shown in FIG. 1, a single dose of doxorubicin caused neurocognitive defects including reduced voluntary wheel running, increased pain, and reduced short term spatial memory. Strikingly, administration of NMN reduced the effects of doxorubicin in all of these measurements, confirming that NMN treatment can at least alleviate neurocognitive defects caused by chemotherapy and/or radiotherapy treatment.

The as-disclosed method may include the use of any other $NAD^+$ precursor for increasing $NAD^+$ level. For example, one could administrate a subject any other $NAD^+$ precursor as appreciated by one skilled in the art to increase $NAD^+$ level in the subject. Some exemplary $NAD^+$ precursors may include tryptophan, quinolinic acid, nicotinic acid, nicotinamide, nicotinamide mononucleotide (NMN) and nicotinamide riboside (NR).

In one embodiment, additional $NAD^+$ precursors may form from dimerization, oligmerization, and polymerization of another known $NAD^+$ precursor, e.g., NMN.

The as-disclosed method may also include the use of any other agents for increasing $NAD^+$ level. In one embodiment, an agent is an enzyme involved in $NAD^+$ biosynthesis, or an enzymatically active fragment thereof, or a nucleic acid encoding an enzyme involved in $NAD^+$ biosynthesis, or an enzymatically active fragment thereof. For example, one may increase $NAD^+$ level in a subject by administering an effective amount of an enzyme involved in $NAD^+$ biosynthesis, or an enzymatically active fragment thereof, or a nucleic acid encoding an enzyme involved in $NAD^+$ biosynthesis, or an enzymatically active fragment thereof.

Enzymes involved in $NAD^+$ biosynthesis may include nicotinate phosphoribosyl transferase 1 (NPT1), pyrazinamidase/nicotinamidase 1 (PNC1), nicotinic acid mononucleotide adenylyltransferase 1 (NMA1), nicotinic acid mononucleotide adenylyltransferase 2 (NMA2), nicotinamide N-methyltransferase (NNMT), nicotinamide phosphoribosyl transferase (NAMPT or NAMPRT), nicotinate/nicotinamide mononucleotide adenylyl transferase 1 (NMNAT-1), nicotinamide mononucleotide adenylyl transferase 2 (NMNAT-2) and nicotinamide mononucleotide adenylyl transferase 3 (NMNAT-3) as described in U.S. Pat. No. 7,977,049, which is incorporated by reference herein.

$NAD^+$ levels may be increased by increasing the activity of enzymes involved in $NAD^+$ biosynthesis (de novo synthesis or salvage pathways). Thus, in one embodiment, the agent of the present invention may be any substance that is capable of increasing the activity of related enzymes. For example, the agent may be any of the activators that are known in the art to activate the related enzymes.

Any means for increasing $NAD^+$ level may be used to prevent or treat short and long term chemotherapy and/or radiotherapy induced peripheral neuropathy and cognitive deficits during chemotherapy and/or radiotherapy administration.

In one embodiment, symptoms of chemotherapy and/or radiotherapy induced peripheral neuropathy (CIPN) may include, but are not limited to, burning, tingling ("pins and needles" feeling), loss of feeling (can be numbness or just less ability to sense pressure, touch, heat, or cold), trouble using fingers to pick up or hold things, dropping things, balance problems, trouble with tripping or stumbling while walking, pressure or temperature hurt more than usual (mostly cold; this is called cold sensitivity), shrinking muscles, muscle weakness, trouble swallowing, constipation, trouble passing urine, blood pressure changes, altered nerve conduction velocity with decreased or no reflexes, cramps, neuromuscular paralysis, and sexual dysfunction. A number of these symptoms are also associated with calcium signaling dysregulation as well.

In one embodiment, typical symptoms of such peripheral neuropathies may include weakness, numbness, paresthesia (abnormal sensations such as burning, tickling, pricking or tingling), sexual dysfunction, and pain in the arms, hands, legs and/or feet. The neuropathy may also be associated with mitochondrial dysfunction. Such neuropathies can exhibit decreased energy levels, i.e. decreased levels of NAD and ATP.

In one specific embodiment, symptoms of CIPN may include tactile & cold allodynia, mechanical and thermal hyperalgesia, short term or long time memory loss, difficulty in spatial cognition, difficulty in executive function, or working memory loss.

The use of chemotherapy and/or radiotherapy agents is well known by one skilled in the art.

To prevent or treat CIPN and cognitive deficits in a subject during chemotherapy and/or radiotherapy administration, the agent of the present invention may be administered to the subject simultaneously with the administration of a chemotherapy agent or right after the administration of a chemotherapy agent, or a period of time after completing chemotherapy and/or radiotherapy.

In one embodiment, a therapeutically effective amount of the agent of the present invention may be co-administered with the chemotherapy agent.

In another embodiment, a therapeutically effective amount of the agent of the present invention may be administered right after the administration of the chemotherapy agent. By the term "right after," we means that the agent is administered to a subject when the subject is still under chemotherapy treatment.

In another embodiment, a therapeutically effective amount of the agent of the present invention may be administered after chemotherapy treatment has ceased, to avoid the possibility that these agents will interfere with chemotherapy efficacy, or increase tumor growth.

In another embodiment, a therapeutically effective amount of the agent of the present invention may be administered to cancer survivors with long term, persistent neuropathic or cognitive problems.

In one embodiment, the present invention discloses a composition or a formulation comprising an agent which is capable of increasing the level of $NAD^+$ in the subject. Such a composition or a formulation additionally includes a pharmaceutically acceptable medium selected from among an excipient, carrier, diluent, and equivalent medium; and a compound as described herein or as appreciated by one skilled in the art.

In one embodiment, the present invention discloses a composition or a formulation for manufacturing a medicament for the treatment and/or prophylaxis of any of the diseases or health conditions disclosed herein. The composition or formulation includes a pharmaceutically acceptable medium selected from among an excipient, carrier, diluent, and equivalent medium; and a compound as described herein or as appreciated by one skilled in the art.

II. Increasing $NAD^+$ Level Reverses Pre-Existing Chemotherapy and/or Radiotherapy Induced Neurocognitive Disorders In one aspect, the present invention is a method for treating and reversing pre-existing CIPN and cognitive deficits by increasing $NAD^+$ level in a subject.

In addition to preventing or treating short and long term CIPN and cognitive deficits during chemotherapy and/or radiotherapy administration, Applicants envision that increasing $NAD^+$ level could also treat or reverse pre-existing CIPN and cognitive deficits in a subject.

In one embodiment, a method for treating or reversing pre-existing CIPN and cognitive deficits in a subject in need thereof comprises the step of administering to the subject an effective amount of an agent that increases the level of $NAD^+$ in the subject.

In one embodiment, the agent is any $NAD^+$ precursor as discussed above or as appreciated by one skilled in the art.

In one specific embodiment, the $NAD^+$ precursor is NMN or a salt thereof, or a prodrug thereof.

In one embodiment, the agent is an enzyme involved in $NAD^+$ biosynthesis, or an enzymatically active fragment thereof, or a nucleic acid encoding an enzyme involved in $NAD^+$ biosynthesis, or an enzymatically active fragment thereof. The enzyme may be any of the enzyme as discussed above or as appreciated by one skilled in the art.

In one specific embodiment, the enzyme is NMNAT-1, NMNAT2, NMNAT3 or NAMPT.

In one embodiment, the agent may also be an activator to an enzyme involved in $NAD^+$ biosynthesis.

In one embodiment, the subject is a human.

To prevent or treat pre-existing CIPN and cognitive deficits in a subject, the agent of the present invention may be administered to the subject after the administration of a chemotherapy agent or radiotherapy. Preferably, the agent of the present invention may be administered after the chemotherapy treatment or radiotherapy.

In one embodiment, the present invention discloses a composition or a formulation comprising an agent which is capable of increasing the level of $NAD^+$ in the subject. Such a composition or a formulation includes a pharmaceutically acceptable medium selected from among an excipient, carrier, diluent, and equivalent medium; and a compound as described herein or as appreciated by one skilled in the art.

In one embodiment, the present invention discloses a composition or a formulation for manufacturing a medicament for the treatment and/or prophylaxis of any of the diseases or health conditions disclosed herein. The composition or formulation includes a pharmaceutically acceptable medium selected from among an excipient, carrier, diluent, and equivalent medium; and a compound as described herein or as appreciated by one skilled in the art.

III. Increasing $NAD^+$ Treats Pain

In one embodiment, the present invention provides a method of administering a therapeutically effective amount of the agent of the present invention to treat or prevent acute or chronic pain including neuropathic pain, either alone or in combination with existing pain treatments. Pain may be induced by factors including but not limited to exposure to certain pharmaceuticals (e.g. chemotherapy), radiation, chemical exposure, wounds, burns, sunburn, shock, explosive shock, electrocution, inflammation, infection, wound healing, high temperature, low temperature, mechanical stress, surgery, neuropathic diseases, malnutrition, drug addiction, drug overdose, or diseases that result in neuropathy and/or pain.

In another embodiment, the agent may be used to treat pain in combination with or in place of painkillers, such as paracetamol, aspirin, ibuprofen, or opioids. Co-administration with the agent as disclosed here may be used to lower the necessary dose of painkillers, and/or improve efficacy, or replace the need for certain painkillers.

In another embodiment, the agent is used to provide resistance to pain.

IV. Increasing NAD$^+$ Treats Cognitive Deficits and Improve Neurocognitive Function In one embodiment, the present invention provides a method for enhancing memory and improving cognitive function in healthy or challenged individuals. Non-limiting examples of cognitive function include processing speed, executive function, attention span and concentration, verbal memory, visual memory, and spatial memory.

In another embodiment, the present invention provides a method for treating any disease related to cognitive deficits. Some exemplary diseases are listed below. However, Applicants envision that the present invention is applicable to any cognitive deficit disease as appreciated by one skilled in the art. Specifically, the present invention provides a method for treating impairments in cognitive function, non-limiting examples of which include processing speed, executive function, attention span and concentration, verbal memory, visual memory and spatial memory.

In another embodiment, the present invention provides a method for preventing and/or treating neurocognitive and/or neurodevelopmental disorders caused by exposure to pollution such as air pollution (e.g., PM 2.5 and PM 10 particles), water pollution, and pollution contamination of food.

In another embodiment, the present invention provides a method for preventing and/or treating neurocognitive deficits and mental health disorders caused by psychological stress, such as combat duty, policing and other environments which may cause post-traumatic stress disorder.

In another embodiment, the present invention provides a method for preventing and/or treating substance abuse and/or addiction.

Essential tremor (ET) is the most common movement disorder. It is a syndrome characterized by a slowly progressive postural and/or kinetic tremor, usually affecting both upper extremities.

Parkinson disease (PD) is a progressive neurodegenerative disorder associated with a loss of dopaminergic nigrostriatal neurons.

Alzheimer disease (AD) is the most common form of dementia. It is a progressive degenerative disease of the brain, strongly associated with advanced age. Over time, people with the disease lose their ability to think and reason clearly, judge situations, solve problems, concentrate, remember useful information, take care of themselves, and even speak. A number of neurodegenerative diseases such as Alzheimer's disease execute their biological impact in the brain. In some embodiments, the disclosed dimers, oligomers and polymers release free compounds that are capable of passing the blood-brain-barrier (BBB).

Huntington disease (HD) is an incurable, adult-onset, autosomal dominant inherited disorder associated with cell loss within a specific subset of neurons in the basal ganglia and cortex.

Ataxia is defined as an inability to maintain normal posture and smoothness of movement. Neurologic symptoms and signs such as seizures and movement disorders (e.g., dystonia, chorea) may accompany ataxia.

Catatonia is a state of apparent unresponsiveness to external stimuli in a person who is apparently awake. Epilepsy is defined as a chronic condition characterized by spontaneous, recurrent seizures; seizure is defined as a clinical event associated with a transient, hypersynchronous neuronal discharge.

Neuroleptic malignant syndrome (NMS) refers to the combination of hyperthermia, rigidity, and autonomic dysregulation that can occur as a serious complication of the use of antipsychotic drugs.

Chorea is an involuntary abnormal movement, characterized by abrupt, brief, nonrhythmic, nonrepetitive movement of any limb, often associated with nonpatterned facial grimaces. Chorea gravidarum (CG) is the term given to chorea occurring during pregnancy.

Cortical basal ganglionic degeneration (CBGD) clinical characteristic include progressive dementia, parkinsonism, and limb apraxia. Dysfunction of the central or peripheral nervous system pathways may cause autonomic dysfunction.

Dystonia is a syndrome of sustained muscle contractions, usually producing twisting and repetitive movements or abnormal postures. Writer's cramp is a form of task-specific focal dystonia.

Mental retardation (MR) is a condition in which intellectual capacity is limited significantly. Developmental disability describes a condition that limits an individual's ability to perform activities and roles as expected in a certain social environment. Frequently, MR and developmental disabilities are present simultaneously as a consequence of brain damage.

Neuroacanthocytosis is a progressive neurologic disease characterized by movement disorders, personality changes, cognitive deterioration, axonal neuropathy, and seizures. Most patients have acanthocytosis on peripheral blood smear at some point during the course of the disease.

Pelizaeus-Merzbacher disease (PMD) and X-linked spastic paraplegia type 2 (SPG2) are at opposite ends of a clinical spectrum of X-linked diseases caused by mutations of the same gene, the proteolipid protein 1 (PLP1) gene, and resulting in defective central nervous system (CNS) myelination. Clinical signs usually include some combination of nystagmus, stridor, spastic quadriparesis, hypotonia, cognitive impairment, ataxia, tremor, and diffuse leukoencephalopathy on MRI scans.

Progressive supranuclear palsy (PSP), also known as Steele-Richardson-Olszewski syndrome, is a neurodegenerative disease that affects cognition, eye movements, and posture.

Striatonigral degeneration (SND) is a neurodegenerative disease that represents a manifestation of multiple system atrophy (MSA). The other manifestations are Shy-Drager syndrome (eg, autonomic failure predominates) and sporadic olivopontocerebellar degeneration (sOPCA, cerebellum predominates).

Ischemic stroke occurs due to a loss of blood supply to part of the brain, initiating the ischemic cascade. Brain tissue ceases to function if deprived of oxygen for more than 60 to 90 seconds and after a few hours will suffer irreversible injury possibly leading to death of the tissue, i.e., infarction. Atherosclerosis may disrupt the blood supply by narrowing the lumen of blood vessels leading to a reduction of blood flow, by causing the formation of blood clots within the vessel, or by releasing showers of small emboli through the disintegration of atherosclerotic plaques. Embolic infarction occurs when emboli formed elsewhere in the circulatory system, typically in the heart as a consequence of atrial fibrilation, or in the carotid arteries. These break off, enter the cerebral circulation, then lodge in and occlude brain blood vessels.

Due to collateral circulation, within the region of brain tissue affected by ischemia there is a spectrum of severity. Thus, part of the tissue may immediately die while other parts may only be injured and could potentially recover. The ischemia area where tissue might recover is referred to as the ischemic penumbra.

As oxygen or glucose becomes depleted in ischemic brain tissue, the production of high energy phosphate compounds such as adenine triphosphate (ATP) fails leading to failure of energy dependent processes necessary for tissue cell survival. This sets off a series of interrelated events that result in cellular injury and death. These include the failure of mitochondria, which can lead further toward energy depletion and may trigger cell death due to apoptosis. Other processes include the loss of membrane ion pump function leading to electrolyte imbalances in brain cells. There is also the release of excitatory neurotransmitters, which have toxic effects in excessive concentrations.

Spinal cord injury, or myelopathy, is a disturbance of the spinal cord that results in loss of sensation and mobility. The two common types of spinal cord injury are: Trauma: automobile accidents, falls, gunshots, diving accidents, etc. Disease: polio, spinabifida, tumors, Friedreich's ataxia, etc. It is important to note that the spinal cord does not have to be completely severed for there to be a loss of function. In fact, the spinal cord remains intact in most cases of spinal cord injury.

Traumatic brain injury (TBI), traumatic injuries to the brain, also called intracranial injury, or simply head injury, occurs when a sudden trauma causes brain damage. TBI can result from a closed head injury or a penetrating head injury and is one of two subsets of acquired brain injury (ABI). The other subset is non-traumatic brain injury (i.e. stroke, meningitis, anoxia). Parts of the brain that can be damaged include the cerebral hemispheres, cerebellum, and brain stem. Symptoms of a TBI can be mild, moderate, or severe, depending on the extent of the damage to the brain. Outcome can be anything from complete recovery to permanent disability or death. A coma can also affect a child's brain. The damage from TBI can be focal, confined to one area of the brain, or diffuse, involving more than one area of the brain. Diffuse trauma to the brain is frequently associated with concussion (a shaking of the brain in response to sudden motion of the head), diffuse axonal injury, or coma. Localized injuries may be associated with neurobehavioral manifestations, hemiparesis or other focal neurologic deficits.

Another insult to the brain that can cause injury is anoxia. Anoxia is a condition in which there is an absence of oxygen supply to an organ's tissues, even if there is adequate blood flow to the tissue. Hypoxia refers to a decrease in oxygen supply rather than a complete absence of oxygen, and ischemia is inadequate blood supply, as is seen in cases in which the brain swells. In any of these cases, without adequate oxygen, a biochemical cascade called the ischemic cascade is unleashed, and the cells of the brain can die within several minutes. This type of injury is often seen in near-drowning victims, in heart attack patients (particularly those who have suffered a cardiac arrest, or in people who suffer significant blood loss from other injuries that then causes a decrease in blood flow to the brain due to circulatory (hypovolemic) shock. Related conditions, such as would occur with severe wound healing or bleed out (e.g., Ebola cytokine storm suppression) can also be treated with the disclosed agents.

Post-chemotherapy cognitive impairment is characterized by temporary or long-lasting neurocognitive deficits, including memory loss, decreased processing speed, loss of executive function, and overall reductions in IQ. These problems are broadly applicable to patients receiving chemotherapy, and are of particular problems to patients who have or are receiving chemotherapy during developmentally important phases (e.g., childhood).

V. Increasing $NAD^+$ to Improve Voluntary Activity, Lethargy, Malaise and Mental Health Disorders In one embodiment, the disclosed agents may be used to increase voluntary physical activity in a healthy individual.

The disclosed agents may be used to increase physical stamina and endurance in a human or animal under healthy, disease challenged or injured state.

The disclosed agents may be used to treat depression or depression like symptoms.

In another embodiment, the disclosed agents may be used to prevent or treat inactivity, lethargy and malaise in an affected individual in need thereof. Non-limiting examples include patients suffering nausea, illness, injury, post-traumatic stress disorder, or mental health disorders.

The disclosed agents may be used to prevent or treat depression or depression like symptoms, including increased risk of self-harm.

The disclosed agents may be used to prevent or treat addictive behaviours such as substance abuse.

The disclosed agents may be used to prevent or treat impaired social development, including verbal and non-verbal communication.

In another example, the disclosed agents may be used to treat psychological and mental health disorders such as depression, anxiety, post-traumatic stress disorders, impaired sleep, circadian rhythm disorders.

In another embodiment, the disclosed agents may be used to treat chemotherapy induced inactivity, lethargy, malaise, and depression.

VI. Pharmaceutical Formulations and Routes of Administration

Pharmaceutical Formulations.

The disclosed agents may be formulated with conventional carriers and excipients, which will be selected in accord with ordinary practice. Tablets may contain excipients, glidants, fillers, binders and the like. Aqueous formulations are prepared in sterile form, and when intended for delivery by other than oral administration generally will be isotonic. All formulations will optionally contain excipients such as those set forth in the "Handbook of Pharmaceutical Excipients" (1986). Possible excipients include ascorbic acid and other antioxidants, chelating agents such as EDTA, carbohydrates such as dextran, hydroxyalkylcellulose, hydroxyalkylmethylcellulose, stearic acid and the like. The pH of the formulations optionally ranges from about 3 to about 11, but is ordinarily about 7 to 10.

The disclosed agents may be formulated with slow release carriers, such as cellulose, ethyl cellulose, hydroxypropyl cellulose, dextran, hyaluronic acid and the like.

While it is possible for the active ingredients to be administered alone it may be preferable to present them as pharmaceutical formulations. The formulations, both for veterinary and for human use, comprise at least one active ingredient, as above defined, together with one or more acceptable carriers therefor and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.). Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then, if necessary, shaping the product.

Formulations of the disclosed agents suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween™ 60, Span™ 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations of the disclosed agents may comprise a combination of one or more such compounds together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally-occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally-occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10%, and particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns, such as 0.5, 1, 30, 35 etc., which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of HCV infections as described below.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations may be presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations may include other agents conventional in the art having regard to the type of formulation in question, for example those suitable for oral administration may include flavoring agents.

The disclosure further provides veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

The disclosed agents are used to provide controlled release pharmaceutical formulations containing as active ingredient one or more compounds of the invention ("controlled release formulations") in which the release of the active ingredient are controlled and regulated to allow less frequency dosing or to improve the pharmacokinetic or toxicity profile of a given active ingredient. In a non-limiting example, the size of the disclosed oligomers and polymers, which can be inversely correlated with rate of release of the therapeutic monomer, may be selected using size exclusion chromatography, filtration though membranes, centrifugation or other methods.

Effective dose of active ingredient depends at least on the nature of the condition being treated, toxicity, whether the compound is being used prophylactically (lower doses) or against an active viral infection, the method of delivery, and the pharmaceutical formulation, and will be determined by the clinician using conventional dose escalation studies. It can be expected to be from about 0.0001 to about 100 mg/kg body weight per day; typically, from about 0.01 to about 10 mg/kg body weight per day; more typically, from about 0.01 to about 5 mg/kg body weight per day; most typically, from about 0.05 to about 0.5 mg/kg body weight per day. For example, the daily candidate dose for an adult human of approximately 70 kg body weight will range from 1 mg to 1000 mg, preferably between 5 mg and 500 mg, and may take the form of single or multiple doses.

Routes of Administration.

One or more of the disclosed agents (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally.

In another embodiment, one of the more disclosed agents is administered during surgery, through topical application to desired areas, intrathecal administration, bathing of tissues in the disclosed agents, or surgical placement of a slow release device, gel, or matrix.

VII. Description of Selected Exemplary Embodiments (Examples)

The following examples are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

Example 1

NAD$^+$ Precursor NMN is Effective in Treating and Preventing Memory Impairments, Inactivity and Allodynia Caused by Doxorubicin In this Example, the strategy is to raise NAD$^+$ levels during chemotherapy treatment by administering animals with a cell permeable NAD$^+$ precursor known as nicotinamide mononucleotide (NMN). NMN is a benign compound, found inside every cell in the body, and is converted in one step to NAD$^+$ by NMNAT enzymes (NMNAT1-3) localized to the nucleus, cytoplasm/golgi and mitochondria, respectively. Given previous investigations of chemotherapy induced memory loss [11-15, 37, 38], it was determined whether NMN could ameliorate neurocognitive deficits caused by doxorubicin, a commonly used anthracycline chemotherapeutic. As expected, a single dose of doxorubicin caused neurocognitive defects including reduced voluntary wheel running, increased pain, and reduced short term spatial memory (FIG. 1). Strikingly, administration of NMN reduced the effects of doxorubicin in all of these measurements, providing evidence for our hypothesis that NMN treatment can alleviate neurocognitive defects caused by chemotherapy treatment.

FIG. 1 demonstrates that Male Sprague-Dawley rats were subjected to baseline testing prior to addition of NMN to drinking water (500 mg/L) 24 prior and 24 hr subsequent to a single i.p. injection of doxorubicin (4 mg/kg) with or without co-administration of NMN (200 mg/kg).

The above data suggest that the NAD$^+$ precursor NMN is effective in treating and preventing memory impairments, inactivity and allodynia caused by doxorubicin.

In a prophetic extension, the NAD+ precursor will also improve other parameters of memory, such as spatial cognition and long term memory, as assessed by a Morris water maze; executive function, as measured by a morris water maze test of reversal learning; and working memory, as assessed by a morris water maze matching to place test.

In addition to mechanical allodynia, inanother prophetic extension, NMN will also provide protection against tactile and thermal allodynia.

In prophetic extension, NMN will provide protection against other chemotherapeutics, such as oxaliplatin or docetaxel.

Example 2

Extension of the Results of Example 1

In this prophetic example, we outline how to extend the above experimental results in four ways. First, we propose that NMN administration post-chemotherapy will be effective in reversing existing neuropathologies associated with CIPN and CICI. Secondly, we propose that mice overexpressing the NAD$^+$ biosynthetic enzymes NMNAT1 and NMNAT3 will be protected against neuropathologies associated with CIPN and CICI. Third, we propose that histological and molecular characterisations of brain and nerve tissues will show that NMN treatment, or NMNAT1 or NMNAT3 over-expression will demonstrate protection against chemotherapy induced cellular apoptosis, necrosis, senescence, inflammation, impaired mitochondrial function, metabolic dysfunction, DNA damage, and other markers of neural damage.

In the above examples, treatment of animals with NAD$^+$ treating compounds will show increased voluntary activity, as measured by a running wheel, laser beam breaks of a metabolic cage, and video monitoring.

Example 3

Testing the Ability of NMN to Increase Physical Activity, Motor Co-Ordination, Stamina and Endurance In this prophetic example, treatment of otherwise healthy animals with an NAD+ raising agent will increase distance run on a treadmill, performance on accelerating rotarod, and voluntary activity.

Example 4

Testing the Ability of NMN to Prevent or Treat Surgical Nerve Damage

In this prophetic example, treatment of otherwise healthy animals with an NAD+ raising agent will increase distance run on a treadmill, performance on accelerating rotarod, and voluntary activity.

Example 5

Investigating the Molecular Response to Chemotherapy in the Brain During NMN Treatment, NMNAT1 and NMNAT3 Over-Expression In this prophetic example, we propose performing a detailed characterization of the molecular pathways through which NMN protects against CIPN and CICI. We will repeat doxorubicin with NMN treatment or in NMNAT1 and NMNAT3 transgenic mice as in Examples 3 and 5, and cull animals one week post doxorubicin to obtain tissues for the molecular analyses described below. For NMN treatment as listed in Hypothetical Example 3, we will use a strain of transgenic reporter mice, which allow non-invasive imaging of cellular senescence caused by toxins such as chemotherapy. We will in addition repeat doxorubicin treatment in NMNAT1 and NMNAT3 transgenic mice and their WT littermates as described in Example 5.

Mitochondrial function will be assessed in freshly isolated brain mitochondria, and activity of each complex of the electrode transport chain will be assessed in a dissolved oxygen Clarke-type electrode as previously described [43] and as shown in FIG. 3. Substrates and inhibitors that are specific for each complex of the electron transport chain will be added, allowing calculation of activity of each complex. These data will be important in pinpointing the nature of any mitochondrial dysfunction, which we expect NMN or NMNAT3 over-expression to reverse as we have found in preliminary data (FIGS. 2B and 3C) and recently published [17].

Apoptosis will be measured through western blotting for cleaved caspase 3 and γH2AX. DNA damage and PARP activity will be assessed by western blotting for poly-ADP ribose (PAR). Immunohistochemical analysis of apoptosis will be assessed as described below.

Gene expression will be profiled in the hippocampus using RNA sequencing to detect coding and non-coding RNA.

Histochemistry:

In some experiments, mice will be perfused with 4% paraformaldehyde under anaesthesia, and the brains removed, post-fixed and sectioned. The tissue will be prepared for histological analysis for pathologies associated with CIPN and CICI. Tissues to be examined will include spinal cord, brain, peripheral nerves, dorsal root ganglia. Tissues will be stained for Ki67 as a marker for neurogenesis, TUNEL as a marker for DNA damage and apoptosis, and GFAP for glial cell activation.

Power Calculations:

The primary outcome for these studies will be complex IV respiratory capacity of brain mitochondria. Assuming an effect size f=0.3, we will need 126 animals per experiment. We will require separate animals for transcardial perfusion of paraformaldehyde for subsequent histological analysis, and will require an additional 94 animals (f=0.35). With NMN treatment, NMNAT1 and NMNAT3 overexpression, we will require 660 mice in total for this aim.

We expect that NMN will protect against chemotherapy induced loss of $NAD^+$, impaired mitochondrial function, neuronal toxicity, cellular senescence, and apoptosis.

Other embodiments and uses will be apparent to those skilled in the art from consideration from the specification and practice of the invention disclosed herein. It is understood that the invention is not confined to the specific reagents, formulations, reaction conditions, etc., herein illustrated and described, but embraces such modified forms thereof as come within the scope of the following claims.

Example 6

Surgical Damage to Neurons

In this prophetic example, mice will be subjected to nerve damage through surgical manipulation.

Before surgical manipulation, mice will be delivered NMN and/or AICAR through i.p. injection, oral gavage or addition to drinking water.

Pain will be assessed post-surgery though various allodynia tests, and it is expected that NMN and/or AICAR pretreatment will prevent nerve damage resulting in pain or neuropathy.

In another prophetic example, NMN is applied to nerves during surgery, and allodynia is assessed afterwards. It is expected that application or implantation of an NMN releasing device during surgery will reduce or prevent nerve damage resulting in pain or neuropathy.

All references cited herein for any reason, including all journal citations and U.S./foreign patents and patent applications, are specifically and entirely incorporated by reference herein.

REFERENCES

1. Haigis, M. C. and D. A. Sinclair, *Mammalian sirtuins: biological insights and disease relevance.* Annu Rev Pathol, 2010. 5: p. 253-95.
2. Munir, F., et al., *Cognitive Intervention for Breast Cancer Patients Undergoing Adjuvant Chemotherapy: A Needs Analysis.* Cancer Nurs, 2011. 34(5): p. 385-92.
3. Boykoff, N., M. Moieni, and S. K. Subramanian, *Confronting chemobrain: an in-depth look at survivors' reports of impact on work, social networks, and health care response.* J Cancer Surviv, 2009. 3(4): p. 223-32.
4. Vardy, J *Cognitive function in breast cancer survivors.* Cancer Treat Res, 2009. 151: p. 387-419.
5. Inagaki, M., et al., *Smaller regional volumes of brain gray and white matter demonstrated in breast cancer survivors exposed to adjuvant chemotherapy.* Cancer, 2007. 109(1): p. 146-56.
6. Silverman, D. H., et al., *Altered frontocortical, cerebellar, and basal ganglia activity in adjuvant-treated breast cancer survivors 5-10 years after chemotherapy.* Breast Cancer Res Treat, 2007. 103(3): p. 303-11.
7. Ferguson, R. J., et al., *Brain structure and function differences in monozygotic twins: possible effects of breast cancer chemotherapy.* J Clin Oncol, 2007. 25(25): p. 3866-70.
8. Seretny, M., et al., *Incidence, prevalence, and predictors of chemotherapy-induced peripheral neuropathy: A systematic review and meta-analysis.* Pain, 2014. 155(12): p. 2461-70.

9. Park, S. B., et al., *Mechanisms underlying chemotherapy-induced neurotoxicity and the potential for neuroprotective strategies*. Curr Med Chem, 2008. 15(29): p. 3081-94.
10. Seigers, R. and J. E. Fardell, *Neurobiological basis of chemotherapy-induced cognitive impairment: a review of rodent research*. Neurosci Biobehav Rev, 2011. 35(3): p. 729-41.
11. Fardell, J. E., J. Vardy, and I. N. Johnston, *Predictors of long-term cognitive outcomes due to oxaliplatin chemotherapy; the role of dose and peripheral neuropathy*. Asia Pacific Journal of Clinical Oncology, 2011. 7(S4): p. 155.
12. Fardell, J. E., J. Vardy, and I. N. Johnston, *The short and long term effects of docetaxel chemotherapy on rodent object recognition and spatial reference memory*. Life Sci, 2013. 93(17): p. 596-604.
13. Fardell, J. E., et al., *Single high dose treatment with methotrexate causes long-lasting cognitive dysfunction in laboratory rodents*. Pharmacol Biochem Behav, 2010. 97(2): p. 333-9.
14. Fardell, J. E., et al., *Cognitive impairments caused by oxaliplatin and 5-fluorouracil chemotherapy are ameliorated by physical activity*. Psychopharmacology (Berl), 2011.
15. Fardell, J. E., et al., *The impact of sustained and intermittent docetaxel chemotherapy regimens on cognition and neural morphology in healthy mice*. Psychopharmacology (Berl), 2013.
16. Dubois, M., et al., *Chemotherapy-induced long-term alteration of executive functions and hippocampal cell proliferation: Role of glucose as adjuvant*. Neuropharmacology, 2013. 79C: p. 234-248.
17. Gomes, A. P., et al., *Declining NAD(+) Induces a Pseudohypoxic State Disrupting Nuclear-Mitochondrial Communication during Aging*. Cell, 2013. 155(7): p. 1624-38.
18. Scheibye-Knudsen, M., et al., *A high-fat diet and NAD(+) activate Sirt1 to rescue premature aging in cockayne syndrome*. Cell Metab, 2014. 20(5): p. 840-55.
19. Meynet, O. and J. E. Ricci, *Caloric restriction and cancer: molecular mechanisms and clinical implications*. Trends Mol Med, 2014. 20(8): p. 419-27.
20. Lagopoulos, L. and R. Stalder, *The influence of food intake on the development of diethylnitrosamine-induced liver tumours in mice*. Carcinogenesis, 1987. 8(1): p. 33-7.
21. Mictchell, S. J., et al., *The SIRT1 activator SRT1720 extends lifespan and improves health of mice fed a standard diet*. Cell Rep., 2014. 6(5): p. 836-43.
22. Mercken, E. M., et al., *SRT2104 extends survival of male mice on a standard diet and preserves bone and muscle mass*. Aging Cell, 2014. 13(5): p. 787-96.
23. Kanfi Y et al *The sirtuin SIRT6 regulates lifespan in male mice* Nature, 2012 483(7388) p 218-21.
24. North, B. J., et al., *SIRT2 induces the checkpoint kinase BubR1 to increase lifespan*. EMBO J, 2014. 33(13): p. 1438-53.
25. Brown, K., et al., *Activation of SIRT3 by the NAD+ precursor nicotinamide riboside protects from noise-induced hearing loss*. Cell Metab, 2014. 20(6): p. 1059-68.
26. Perry, V. H., et al., *Evidence that the Rate of Wallerian Degeneration is Controlled by a Single Autosomal Dominant Gene*. Eur J Neurosci, 1990. 2(5): p. 408-13.
27. Mack, T. G., et al., *Wallerian degeneration of injured axons and synapses is delayed by a Ube4b/Nmnat chimeric gene*. Nat Neurosci, 2001. 4(12): p. 1199-206.
28. Sasaki, Y., et al., *Transgenic mice expressing the Nmnat1 protein manifest robust delay in axonal degeneration in vivo*. J Neurosci, 2009. 29(20): p. 6526-34.
29. Kitaoka, Y., et al., *Axonal protection by Nmnat3 overexpression with involvement of autophagy in optic nerve degeneration*. Cell Death Dis, 2013. 4: p. e860.
30. Spronck, J. C. and J. B. Kirkland, *Niacin deficiency increases spontaneous and etoposide-induced chromosomal instability in rat bone marrow cells in vivo*. Mutat Res, 2002. 508(1-2): p. 83-97.
31. Spronck, J. C., J. L. Nickerson, and J. B. Kirkland, *Niacin deficiency alters p53 expression and impairs etoposide-induced cell cycle arrest and apoptosis in rat bone marrow cells*. Nutr Cancer, 2007. 57(1): p. 88-99.
32. Kostecki, L. M., et al., *Niacin deficiency delays DNA excision repair and increases spontaneous and nitrosourea-induced chromosomal instability in rat bone marrow*. Mutat Res, 2007. 625(1-2): p. 50-61.
33. Oh, G. S., et al., *Pharmacological activation of NQO1 increases NAD(+) levels and attenuates cisplatin-mediated acute kidney injury in mice*. Kidney Int, 2014. 85(3): p. 547-60.
34. Kim, H. J., et al., *Augmentation of NAD(+) by NQO1 attenuates cisplatin-mediated hearing impairment*. Cell Death Dis, 2014. 5: p. e1292.
35. Wang, G., et al., *P7C3 Neuroprotective Chemicals Function by Activating the Rate-Limiting Enzyme in NAD Salvage*. Cell, 2014. 158(6): p. 1324-34.
36. Bitterman, K. J., et al., *Inhibition of silencing and accelerated aging by nicotinamide, a putative negative regulator of yeast sir2 and human SIRT1*. J Biol Chem, 2002. 277(47): p. 45099-107.
37. Fardell, J. E., et al., *Cognitive impairment in mice following chemotherapy; a comparison of continuous versus intermittent docetaxel treatment*. Asia-Pacific Journal of Clinical Oncology, 2010. 6(S3): p. 237.
38. Sharpe, M. J., et al., *The chemotherapy agent oxaliplatin impairs the renewal of fear to an extinguished conditioned stimulus in rats*. Behav Brain Res, 2012. 227(1): p. 295-9.
39. Wu, L. E., A. P. Gomes, and D. A. Sinclair, *Geroncogenesis: metabolic changes during aging as a driver of tumorigenesis*. Cancer Cell, 2014. 25(1): p. 12-9.
40. Fardell, J. E et al., *Cognitive impairments caused by oxaliplatin and 5-fluorouracil chemotherapy are ameliorated by physical activity*. Psychopharmacology (Berl), 2012. 220(1): p. 183-93.
41. Aggleton, J. P. and M. W. Brown, *Contrasting hippocampal and perirhinal cortex function using immediate early gene imaging*. Q J Exp Psychol B, 2005. 58(3-4): p. 218-33.
42. Winocur, G., et al., *Physical exercise prevents suppression of hippocampal neurogenesis and reduces cognitive impairment in chemotherapy-treated rats*. Psychopharmacology (Berl), 2014. 231(11): p. 2311-20.
43. Kuznetsov, A. V., et al., *Analysis of mitochondrial function in situ in permeabilized muscle fibers, tissues and cells*. Nat Protoc, 2008. 3(6): p. 965-76.
44. Burd, C. E., et al., *Monitoring tumorigenesis and senescence in vivo with a p16(INK4a)-luciferase model*. Cell, 2013. 152(1-2): p. 340-51.
45. Sorrentino, J. A., et al., *p16INK4a reporter mice reveal age promoting effects of environmental toxicants*. J Clin Invest, 2014. 124(1): p. 169-73.
46. Zhao, K., et al., *Cancer survival and prevalence in Australia. Cancers diagnosed from 1982 to 2004*, in *Cancer Series*. 2008, Australian Institute of Health and Welfare.

47. Argyriou, A. A., et al., *A review on oxaliplatin-induced peripheral nerve damage.* Cancer Treat Rev, 2008. 34(4): p. 368-77.

48. Swain, S. M. and J. C. Arezzo, *Neuropathy associated with microtubule inhibitors: diagnosis, incidence, and management.* Clin Adv Hematol Oncol, 2008. 6(6): p. 455-67.

The invention claimed is:

1. A method for treating radiation-induced neurotoxic damage in a subject, comprising administering to a subject who has undergone exposure to radiation as a form of radiotherapy, is undergoing exposure to radiation as a form of radiotherapy, or will undergo exposure to radiation as a form of radiotherapy, an effective amount of an agent that increases the level of NAD+ in the subject, whereby radiation-induced neurotoxic damage is prophylactically treated,
wherein the agent that increases the level of NAD+ in the subject is an NAD+ precursor selected from nicotinamide mononucleotide (NMN), nicotinic acid, nicotinamide, nicotinamide riboside (NR), nicotinic acid mononucleotide, nicotinic acid riboside, 5-aminoimidazole-4-carboxamide ribonucleotide (AICAR), adenosine, adenine, and adenosine monophosphate, or a salt thereof.

2. The method of claim 1, wherein the radiation-induced neurotoxic damage comprises radiation-induced cognitive impairments.

3. The method of claim 1, wherein the radiation-induced neurotoxic damage comprises pain and/or radiation-induced peripheral neuropathies.

4. The method of claim 1, wherein the radiation-induced neurotoxic damage comprises radiation-induced inactivity.

5. The method of claim 1, wherein the radiation-induced neurotoxic damage comprises radiation-induced depression, anxiety, melancholy, post-traumatic stress disorder, impaired sleep, or a circadian rhythm disorder.

6. The method of claim 1, wherein the agent that increases the level of NAD+ in the subject is administered at the same time as the subject undergoes exposure to radiation as a form of radiotherapy.

7. The method of claim 1, wherein the radiation-induced neurotoxic damage comprises inactivity, lethargy, or malaise, or a combination thereof.

8. The method of claim 1, wherein the radiation-induced neurotoxic damage comprises depression, anxiety, melancholy, or post-traumatic stress disorder.

9. The method of claim 1, wherein the exposure to radiation comprises exposure to $\alpha$, $\beta$, and $\gamma$-irradiation through direct irradiation or administration of radiation emitting isotopes, or a combination thereof.

10. The method of claim 1, wherein the agent that increases the level of NAD+ is an activator to an enzyme involved in NAD+ biosynthesis.

11. The method of claim 1, wherein the agent that increases the level of NAD+ is administered at a dose of 0.5-5 grams per day.

12. The method of claim 1, wherein the subject is a human.

13. The method of claim 1, comprising administering the agent that increases the level of NAD+ in the subject before the subject undergoes exposure to radiation as a form of radiotherapy.

14. The method of claim 1, comprising administering the agent that increases the level of NAD+ in the subject after the subject undergoes exposure to radiation as a form of radiotherapy.

\* \* \* \* \*